United States Patent
Little, II

(10) Patent No.: US 6,436,660 B1
(45) Date of Patent: *Aug. 20, 2002

(54) IDENTIFICATION OF NOVEL ANTIMICROBIAL AGENTS USING METABOLIC OXIDATION-REDUCTION INDICATOR DYES

(75) Inventor: Roger G. Little, II, Benicia, CA (US)

(73) Assignee: XOMA Technology Ltd., Berkeley, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/543,955

(22) Filed: Apr. 6, 2000

Related U.S. Application Data

(60) Provisional application No. 60/143,290, filed on Jul. 12, 1999.

(51) Int. Cl.[7] .............................. C12Q 1/18; C12Q 1/26; C12Q 1/00
(52) U.S. Cl. .............................. 435/32; 435/25; 435/4; 435/254.1; 435/968
(58) Field of Search .............................. 435/32, 29, 4, 435/968, 254.1, 25

(56) References Cited

U.S. PATENT DOCUMENTS 5,858,974 A * 1/1999 Little, II et al. .............. 514/12
6,143,516 A * 11/2000 Little, II et al. .............. 435/29
6,156,730 A * 12/2000 Little, II et al. .............. 514/14

OTHER PUBLICATIONS

Georgopapadakou, N. H., et al. "Antifungal Agents: Chemotherapeutic Targets and Immunologic Strategies," *Antimicrobial Agents and Chemotherapy*, 40 (2): 279–291 (1996).

Monk, B. C. et al., "Fungal Plasma Membrane Proton Pumps as Promising New Antifungal Targets," *Critical Reviews in Microbiology*, 20(3):209–223 (1994).

Portillo, F., et al., "Mode of Action of Miconazole on Yeasts: Inhibition of the Mitochondrial ATPase," *European Journal of Biochemistry*, 143(2):273–276 (1984).

Odds, F.C. "Antifungal Agents and Their Use in *Candida* Infections," In: Candida and Candidosis, Chapter 27, pp. 279–313 (1979).

Baker, C.N. et al., "Evaluation of Alamar colorimetric MIC method for antimicrobial susceptibility testing of gram–negative bacteria bacteria," *Journal of Clinical Microbiology*, 32(5):1261–1267 (1994).

Baker, C.N. et al., Chemical Abstracts, vol. 121, No. 9, abstract No. 103914, XP002143871, Columbus, OH, US (Aug. 29, 1994) (Abstract).

* cited by examiner

Primary Examiner—Louise N. Leary
(74) Attorney, Agent, or Firm—Marshall, Gerstein & Borun

(57) ABSTRACT

Novel screening methods for identifying antimicrobial agents involving use of metabolic oxidation-reduction indicator dyes are provided.

8 Claims, 8 Drawing Sheets

*Several points were at the limits of the plate reader and were assigned the value of 10,000

SEQUENCE LISTING

<160> NUMBER OF SEQ ID NOS: 6

<210> SEQ ID NO 1
<211> LENGTH: 1813
<212> TYPE: DNA
<213> ORGANISM: Homo sapiens
<220> FEATURE:
<221> NAME/KEY: CDS
<222> LOCATION: (31)..(1491)
<220> FEATURE:
<221> NAME/KEY: mat_peptide
<222> LOCATION: (124)..(1491)

<400> SEQUENCE: 1

```
caggccttga ggttttggca gctctggagg atg aga gag aac atg gcc agg ggc          54
                                Met Arg Glu Asn Met Ala Arg Gly
                                -30                 -25 cct tgc aac gcg ccg aga tgg gtg tcc ctg atg gtg ctc gtc gcc ata         102
Pro Cys Asn Ala Pro Arg Trp Val Ser Leu Met Val Leu Val Ala Ile
            -20                 -15                 -10 ggc acc gcc gtg aca gcg gcc gtc aac cct ggc gtc gtg gtc agg atc         150
Gly Thr Ala Val Thr Ala Ala Val Asn Pro Gly Val Val Val Arg Ile
         -5              -1   1                   5 tcc cag aag ggc ctg gac tac gcc agc cag cag ggg acg gcc gct ctg         198
Ser Gln Lys Gly Leu Asp Tyr Ala Ser Gln Gln Gly Thr Ala Ala Leu
 10                  15                  20                  25 cag aag gag ctg aag agg atc aag att cct gac tac tca gac agc ttt         246
Gln Lys Glu Leu Lys Arg Ile Lys Ile Pro Asp Tyr Ser Asp Ser Phe
                 30                  35                  40 aag atc aag cat ctt ggg aag ggg cat tat agc ttc tac agc atg gac         294
Lys Ile Lys His Leu Gly Lys Gly His Tyr Ser Phe Tyr Ser Met Asp
             45                  50                  55 atc cgt gaa ttc cag ctt ccc agt tcc cag ata agc atg gtg ccc aat         342
Ile Arg Glu Phe Gln Leu Pro Ser Ser Gln Ile Ser Met Val Pro Asn
         60                  65                  70 gtg ggc ctt aag ttc tcc atc agc aac gcc aat atc aag atc agc ggg         390
Val Gly Leu Lys Phe Ser Ile Ser Asn Ala Asn Ile Lys Ile Ser Gly
     75                  80                  85 aaa tgg aag gca caa aag aga ttc tta aaa atg agc ggc aat ttt gac         438
Lys Trp Lys Ala Gln Lys Arg Phe Leu Lys Met Ser Gly Asn Phe Asp
 90                  95                 100                 105 ctg agc ata gaa ggc atg tcc att tcg gct gat ctg aag ctg ggc agt         486
Leu Ser Ile Glu Gly Met Ser Ile Ser Ala Asp Leu Lys Leu Gly Ser
                110                 115                 120 aac ccc acg tca ggc aag ccc acc atc acc tgc tcc agc tgc agc agc         534
Asn Pro Thr Ser Gly Lys Pro Thr Ile Thr Cys Ser Ser Cys Ser Ser
            125                 130                 135 cac atc aac agt gtc cac gtg cac atc tca aag agc aaa gtc ggg tgg         582
His Ile Asn Ser Val His Val His Ile Ser Lys Ser Lys Val Gly Trp
        140                 145                 150 ctg atc caa ctc ttc cac aaa aaa att gag tct gcg ctt cga aac aag         630
Leu Ile Gln Leu Phe His Lys Lys Ile Glu Ser Ala Leu Arg Asn Lys
    155                 160                 165 atg aac agc cag gtc tgc gag aaa gtg acc aat tct gta tcc tcc aag         678
Met Asn Ser Gln Val Cys Glu Lys Val Thr Asn Ser Val Ser Ser Lys
170                 175                 180                 185 ctg caa cct tat ttc cag act ctg cca gta atg acc aaa ata gat tct         726
Leu Gln Pro Tyr Phe Gln Thr Leu Pro Val Met Thr Lys Ile Asp Ser
                190                 195                 200 gtg gct gga atc aac tat ggt ctg gtg gca cct cca gca acc acg gct         774
Val Ala Gly Ile Asn Tyr Gly Leu Val Ala Pro Pro Ala Thr Thr Ala
```

```
                Val Ala Gly Ile Asn Tyr Gly Leu Val Ala Pro Pro Ala Thr Thr Ala
                            205                 210                 215 gag acc ctg gat gta cag atg aag ggg gag ttt tac agt gag aac cac                  822
Glu Thr Leu Asp Val Gln Met Lys Gly Glu Phe Tyr Ser Glu Asn His
            220                 225                 230 cac aat cca cct ccc ttt gct cca cca gtg atg gag ttt ccc gct gcc                  870
His Asn Pro Pro Pro Phe Ala Pro Pro Val Met Glu Phe Pro Ala Ala
        235                 240                 245 cat gac cgc atg gta tac ctg ggc ctc tca gac tac ttc ttc aac aca                  918
His Asp Arg Met Val Tyr Leu Gly Leu Ser Asp Tyr Phe Phe Asn Thr
250                 255                 260                 265 gcc ggg ctt gta tac caa gag gct ggg gtc ttg aag atg acc ctt aga                  966
Ala Gly Leu Val Tyr Gln Glu Ala Gly Val Leu Lys Met Thr Leu Arg
                270                 275                 280 gat gac atg att cca aag gag tcc aaa ttt cga ctg aca acc aag ttc                 1014
Asp Asp Met Ile Pro Lys Glu Ser Lys Phe Arg Leu Thr Thr Lys Phe
            285                 290                 295 ttt gga acc ttc cta cct gag gtg gcc aag aag ttt ccc aac atg aag                 1062
Phe Gly Thr Phe Leu Pro Glu Val Ala Lys Lys Phe Pro Asn Met Lys
        300                 305                 310 ata cag atc cat gtc tca gcc tcc acc ccg cca cac ctg tct gtg cag                 1110
Ile Gln Ile His Val Ser Ala Ser Thr Pro Pro His Leu Ser Val Gln
    315                 320                 325 ccc acc ggc ctt acc ttc tac cct gcc gtg gat gtc cag gcc ttt gcc                 1158
Pro Thr Gly Leu Thr Phe Tyr Pro Ala Val Asp Val Gln Ala Phe Ala
330                 335                 340                 345 gtc ctc ccc aac tcc tcc ctg gct tcc ctc ttc ctg att ggc atg cac                 1206
Val Leu Pro Asn Ser Ser Leu Ala Ser Leu Phe Leu Ile Gly Met His
                350                 355                 360 aca act ggt tcc atg gag gtc agc gcc gag tcc aac agg ctt gtt gga                 1254
Thr Thr Gly Ser Met Glu Val Ser Ala Glu Ser Asn Arg Leu Val Gly
            365                 370                 375 gag ctc aag ctg gat agg ctg ctc ctg gaa ctg aag cac tca aat att                 1302
Glu Leu Lys Leu Asp Arg Leu Leu Leu Glu Leu Lys His Ser Asn Ile
        380                 385                 390 ggc ccc ttc ccg gtt gaa ttg ctg cag gat atc atg aac tac att gta                 1350
Gly Pro Phe Pro Val Glu Leu Leu Gln Asp Ile Met Asn Tyr Ile Val
    395                 400                 405 ccc att ctt gtg ctg ccc agg gtt aac gag aaa cta cag aaa ggc ttc                 1398
Pro Ile Leu Val Leu Pro Arg Val Asn Glu Lys Leu Gln Lys Gly Phe
410                 415                 420                 425 cct ctc ccg acg ccg gcc aga gtc cag ctc tac aac gta gtg ctt cag                 1446
Pro Leu Pro Thr Pro Ala Arg Val Gln Leu Tyr Asn Val Val Leu Gln
                430                 435                 440 cct cac cag aac ttc ctg ctg ttc ggt gca gac gtt gtc tat aaa                     1491
Pro His Gln Asn Phe Leu Leu Phe Gly Ala Asp Val Val Tyr Lys
            445                 450                 455 tgaaggcacc agggtgccg ggggctgtca gccgcacctg ttcctgatgg gctgtggggc                1551
accggctgcc tttccccagg gaatcctctc cagatcttaa ccaagagccc cttgcaaact               1611
tcttcgactc agattcagaa atgatctaaa cacgaggaaa cattattcat tggaaaagtg               1671
catggtgtgt attttaggga ttatgagctt cttcaagggg ctaaggctgc agagatattt               1731
cctccaggaa tcgtgtttca attgtaacca agaaatttcc atttgtgctt catgaaaaaa               1791
aacttctggt tttttcatg tg                                                         1813

<210> SEQ ID NO 2
<211> LENGTH: 487
<212> TYPE: PRT
```

<213> ORGANISM: Homo sapiens

<400> SEQUENCE: 2

```
Met Arg Glu Asn Met Ala Arg Gly Pro Cys Asn Ala Pro Arg Trp Val
    -30             -25                 -20

Ser Leu Met Val Leu Val Ala Ile Gly Thr Ala Val Thr Ala Val
-15             -10                  -5                  -1   1

Asn Pro Gly Val Val Arg Ile Ser Gln Lys Gly Leu Asp Tyr Ala
             5                  10                  15

Ser Gln Gln Gly Thr Ala Ala Leu Gln Lys Glu Leu Lys Arg Ile Lys
            20                  25                  30

Ile Pro Asp Tyr Ser Asp Ser Phe Lys Ile Lys His Leu Gly Lys Gly
            35                  40                  45

His Tyr Ser Phe Tyr Ser Met Asp Ile Arg Glu Phe Gln Leu Pro Ser
 50                  55                  60                  65

Ser Gln Ile Ser Met Val Pro Asn Val Gly Leu Lys Phe Ser Ile Ser
                 70                  75                  80

Asn Ala Asn Ile Lys Ile Ser Gly Lys Trp Lys Ala Gln Lys Arg Phe
             85                  90                  95

Leu Lys Met Ser Gly Asn Phe Asp Leu Ser Ile Glu Gly Met Ser Ile
            100                 105                 110

Ser Ala Asp Leu Lys Leu Gly Ser Asn Pro Thr Ser Gly Lys Pro Thr
    115                 120                 125

Ile Thr Cys Ser Ser Cys Ser Ser His Ile Asn Ser Val His Val His
130                 135                 140                 145

Ile Ser Lys Ser Lys Val Gly Trp Leu Ile Gln Leu Phe His Lys Lys
                150                 155                 160

Ile Glu Ser Ala Leu Arg Asn Lys Met Asn Ser Gln Val Cys Glu Lys
            165                 170                 175

Val Thr Asn Ser Val Ser Ser Lys Leu Gln Pro Tyr Phe Gln Thr Leu
            180                 185                 190

Pro Val Met Thr Lys Ile Asp Ser Val Ala Gly Ile Asn Tyr Gly Leu
    195                 200                 205

Val Ala Pro Pro Ala Thr Thr Ala Glu Thr Leu Asp Val Gln Met Lys
210                 215                 220                 225

Gly Glu Phe Tyr Ser Glu Asn His His Asn Pro Pro Phe Ala Pro
                230                 235                 240

Pro Val Met Glu Phe Pro Ala Ala His Asp Arg Met Val Tyr Leu Gly
            245                 250                 255

Leu Ser Asp Tyr Phe Phe Asn Thr Ala Gly Leu Val Tyr Gln Glu Ala
            260                 265                 270

Gly Val Leu Lys Met Thr Leu Arg Asp Asp Met Ile Pro Lys Glu Ser
    275                 280                 285

Lys Phe Arg Leu Thr Thr Lys Phe Phe Gly Thr Phe Leu Pro Glu Val
290                 295                 300                 305

Ala Lys Lys Phe Pro Asn Met Lys Ile Gln Ile His Val Ser Ala Ser
                310                 315                 320

Thr Pro Pro His Leu Ser Val Gln Pro Thr Gly Leu Thr Phe Tyr Pro
            325                 330                 335

Ala Val Asp Val Gln Ala Phe Ala Val Leu Pro Asn Ser Ser Leu Ala
            340                 345                 350

Ser Leu Phe Leu Ile Gly Met His Thr Thr Gly Ser Met Glu Val Ser
    355                 360                 365
```

```
                            -continued

Ala Glu Ser Asn Arg Leu Val Gly Glu Leu Lys Leu Asp Arg Leu Leu
370                 375                 380                 385

Leu Glu Leu Lys His Ser Asn Ile Gly Pro Phe Pro Val Glu Leu Leu
                390                 395                 400

Gln Asp Ile Met Asn Tyr Ile Val Pro Ile Leu Val Leu Pro Arg Val
                405                 410                 415

Asn Glu Lys Leu Gln Lys Gly Phe Pro Leu Pro Thr Pro Ala Arg Val
            420                 425                 430

Gln Leu Tyr Asn Val Val Leu Gln Pro His Gln Asn Phe Leu Leu Phe
        435                 440                 445

Gly Ala Asp Val Val Tyr Lys
450                 455

<210> SEQ ID NO 3
<211> LENGTH: 10
<212> TYPE: PRT
<213> ORGANISM: Artificial Sequence
<220> FEATURE:
<223> OTHER INFORMATION: Description of Artificial Sequence: artificial
      peptide XMP.365
<220> FEATURE:
<221> NAME/KEY: SITE
<222> LOCATION: (1)..(10)
<223> OTHER INFORMATION: Positions 1-10 are D-amino acids
<220> FEATURE:
<223> OTHER INFORMATION: The C-Terminus is Amidated

<400> SEQUENCE: 3

Lys Trp Leu Ile Gln Leu Phe His Lys Lys
 1               5                  10

<210> SEQ ID NO 4
<211> LENGTH: 12
<212> TYPE: PRT
<213> ORGANISM: Artificial Sequence
<220> FEATURE:
<223> OTHER INFORMATION: Description of Artificial Sequence: artificial
      peptide XMP.391
<220> FEATURE:
<223> OTHER INFORMATION: The C-Terminus is Amidated

<400> SEQUENCE: 4

Lys Val Gly Trp Leu Ile Gln Leu Phe His Lys Lys
 1               5                  10

<210> SEQ ID NO 5
<211> LENGTH: 10
<212> TYPE: PRT
<213> ORGANISM: Artificial Sequence
<220> FEATURE:
<223> OTHER INFORMATION: Description of Artificial Sequence: artificial
      peptide XMP.416
<220> FEATURE:
<221> NAME/KEY: SITE
<222> LOCATION: (1)..(10)
<223> OTHER INFORMATION: Positions 1-10 are D-amino acids
<220> FEATURE:
<223> OTHER INFORMATION: The C-Terminus is Amidated
<220> FEATURE:
<223> OTHER INFORMATION: 8-amino-octanyl group; $NH_2$-$(CH_2)_7$-CO at
      N-Terminus

<400> SEQUENCE: 5

Lys Trp Leu Ile Gln Leu Phe His Lys Lys
 1               5                  10

<210> SEQ ID NO 6
```

```
<211> LENGTH: 12
<212> TYPE: PRT
<213> ORGANISM: Artificial Sequence
<220> FEATURE:
<223> OTHER INFORMATION: Description of Artificial Sequence: artificial
      peptide XMP.445
<220> FEATURE:
<221> NAME/KEY: SITE
<222> LOCATION: (1)
<223> OTHER INFORMATION: At position 1, Xaa=D-Lys
<220> FEATURE:
<221> NAME/KEY: SITE
<222> LOCATION: (2)
<223> OTHER INFORMATION: At position 2, Xaa=D-Val
<220> FEATURE:
<221> NAME/KEY: SITE
<222> LOCATION: (11)
<223> OTHER INFORMATION: At position 11, Xaa=D-Lys
<220> FEATURE:
<221> NAME/KEY: SITE
<222> LOCATION: (12)
<223> OTHER INFORMATION: At position 12, Xaa=D-Lys

<400> SEQUENCE: 6

Xaa Xaa Gly Trp Leu Ile Gln Leu Phe His Xaa Xaa
 1               5                  10
```

IDENTIFICATION OF NOVEL ANTIMICROBIAL AGENTS USING METABOLIC OXIDATION-REDUCTION INDICATOR DYES

This application claims priority of U.S. Provisional Application Ser. No. 60/143,290 filed Jul. 12, 1999, the disclosure of which is incorporated by reference herein.

FIELD OF THE INVENTION

The invention relates generally to screening methods involving use of metabolic oxidation-reduction indicator dyes for identifying antimicrobial agents.

BACKGROUND OF THE INVENTION

Infectious diseases can be caused by a number of organisms, including bacteria, fungi, protozoans and other parasites, and viruses. Bacteria as a group generally include gram-negative bacteria, gram-positive bacteria, spirochetes, rickettsiae, mycoplasmas, mycobacteria and actinomycetes. Resistance of bacteria and other pathogenic organisms to antimicrobial agents is an increasingly troublesome problem. The accelerating development of antibiotic-resistant bacteria, intensified by the widespread use of antibiotics in farm animals and overprescription of antibiotics by physicians, has been accompanied by declining research into new antibiotics with different modes of action. [*Science,* 264: 360–374 (1994).]

Antibacterial agents can be broadly classified based on chemical structure and proposed mechanism of action, and major groups include the following: (1) the β-lactams, including the penicillins, cephalosporins and monobactams; (2) the aminoglycosides, e.g., gentamicin, tobramycin, netilmycin, and amikacin; (3) the tetracyclines; (4) the sulfonamides and trimethoprim; (5) the fluoroquinolones, e.g., ciprofloxacin, norfloxacin, and ofloxacin; (6) vancomycin; (7) the macrolides, which include for example, erythromycin, azithromycin, and clarithromycin; and (8) other antibiotics, e.g., the polymyxins, chloramphenicol and the lincosamides.

Antibiotics accomplish their anti-bacterial effect through several mechanisms of action which can be generally grouped as follows: (1) agents acting on the bacterial cell wall such as bacitracin, the cephalosporins, cycloserine, fosfomycin, the penicillins, ristocetin, and vancomycin; (2) agents affecting the cell membrane or exerting a detergent effect, such as colistin, novobiocin and polymyxins; (3) agents affecting cellular mechanisms of replication, information transfer, and protein synthesis by their effects on ribosomes, e.g., the aminoglycosides, the tetracyclines, chloramphenicol, clindamycin, cycloheximide, fucidin, lincomycin, puromycin, rifampicin, other streptomycins, and the macrolide antibiotics such as erythromycin and oleandomycin; (4) agents affecting nucleic acid metabolism, e.g., the fluoroquinolones, actinomycin, ethambutol, 5-fluorocytosine, griseofulvin, rifamycins; and (5) drugs affecting intermediary metabolism, such as the sulfonamides, trimethoprim, and the tuberculostatic agents isoniazid and para-aminosalicylic acid. Some agents may have more than one primary mechanism of action, especially at high concentrations. In addition, secondary changes in the structure or metabolism of the bacterial cell often occur after the primary effect of the antimicrobial drug.

Protozoa account for a major proportion of infectious diseases worldwide, but most protozoan infections occur in developing countries. Treatment of protozoan infections is hampered by a lack of effective chemotherapeutic agents, excessive toxicity of the available agents, and developing resistance to these agents.

Fungi are not only important human and animal pathogens, but they are also among the most common causes of plant disease. Fungal infections (mycoses) are becoming a major concern for a number of reasons, including the limited number of antifungal agents available, the increasing incidence of species resistant to known antifungal agents, and the growing population of immunocompromised patients at risk for opportunistic fungal infections, such as organ transplant patients, cancer patients undergoing chemotherapy, burn patients, AIDS patients, or patients with diabetic ketoacidosis. The incidence of systemic fungal infections increased 600% in teaching hospitals and 220% in non-teaching hospitals during the 1980's. The most common clinical isolate isolated is *Candida albicans* (comprising about 19% of all isolates). In one study, nearly 40of all deaths from hospital-acquired infections were due to fungi. [Sternberg, *Science,* 266:1632–1634 (1994).].

Known antifungal agents include polyene derivatives, such as amphotericin B (including lipid or liposomal formulations thereof) and the structurally related compounds nystatin and pimaricin; flucytosile (5-fluorocytosine); azole derivatives (including ketoconazole, clotrimazole, miconazole, econazole, butoconazole, oxiconazole, sulconazole, tioconazole, terconazole, fluconazole, itraconazole, voriconazole [Pfizer], poscaconazole [SCH56592, Schering-Plough]) and ravuconazole; allylamines-thiocarbamates (including tolnaftate, naftifine and terbinafine); griseofulvin; ciclopirox; haloprogin; echinocandins (including caspofungin [MK-0991, Merck], FK463 [Fujisawa] and VER-002 [Versicor]); nikkomycins; and sordarins. Recently discovered as antifungal agents are a class of products related to bactericidal permneability-increasing protein (BPI), described in U.S. Pat. Nos. 5,627,153, 5,858,974, 5,652,332, 5,856,438, 5,763,567 and 5,733,872, the disclosures of all of which are incorporated herein by reference.

Bactericidal/permeability-increasing protein (BPI) is a protein isolated from the granules of mammalian polymorphonuclear leukocytes (PMNs or neutrophils), which are blood cells essential in the defense against invading microorganisms. See Elsbach, 1979, *J. Biol. Chem.,* 254: 11000; Weiss et al., 1987, *Blood* 69: 652; Gray et al., 1989, *J Biol. Chem.* 264: 9505. The amino acid sequence of the entire human BPI protein and the nucleic acid sequence of DNA encoding the protein (SEQ ID NOS: 1 and 2) have been reported in U.S. Pat. No. 5,198,541 and FIG. 1 of Gray et al., *J. Biol. Chem.,* 264:9505 (1989), incorporated herein by reference. Recombinant human BPI holoprotein has also been produced in which valine at position 151 is specified by GTG rather than GTC, residue 185 is glutamic acid (specified by GAG) rather than lysine (specified by AAG) and residue 417 is alanine (specified by GCT) rather than valine (specified by GTT). An N-terminal fragment of human BPI possesses the anti-bacterial efficacy of the naturally-derived 55 kD human BPI holoprotein. (Ooi et al., 1987, *J. Bio. Chem.* 262: 14891–14894). In contrast to the N-terminal portion, the C-terminal region of the isolated human BPI protein displays only slightly detectable anti-bacterial activity against gram-negative organisms and some endotoxin neutralizing activity. (Ooi et al., 1991, *J. Exp. Med.* 174: 649). An N-terminal BPI fragment of approximately 23 kD, referred to as rBPI$_{23}$, has been produced by recombinant means and also retains anti-bacterial, including anti-endotoxin activity against gram-negative organisms (Gazzano-Santoro et al., 1992, *Infect. Immun.* 60: 4754–4761). An N-terminal analog designated rBPI$_{21}$ (also referred to as rBPI(1-193)ala$^{132}$) has been described in U.S. Pat. No. 5,420,019.

Three separate functional domains within the recombinant 23 kD N-terminal BPI sequence have been discovered (Little et al., 1994, *J. Biol. Chem.* 269: 1865). These functional domains of BPI designate regions of the amino acid sequence of BPI that contributes to the total biological activity of the protein and were essentially defined by the activities of proteolytic cleavage fragments, overlapping 15-mer peptides and other synthetic peptides. Domain I is defined as the amino acid sequence of BPI comprising from about amino acid 17 to about amino acid 45. Initial peptides based on this domain were moderately active in both the inhibition of LPS-induced LAL activity and in heparin binding assays, and did not exhibit significant bactericidal activity. Domain II is defined as the amino acid sequence of BPI comprising from about amino acid 65 to about amino acid 99. Initial peptides based on this domain exhibited high LPS and heparin binding capacity and exhibited significant antibacterial activity. Domain III is defined as the amino acid sequence of BPI comprising from about amino acid 142 to about amino acid 169. Initial peptides based on this domain exhibited high LPS and heparin binding activity and exhibited surprising antimicrobial activity, including antifungal and antibacterial (including, e.g., anti-gram-positive and anti-gram-negative) activity. The biological activities of peptides derived from or based on these functional domains (i.e., functional domain peptides) may include LPS binding, LPS neutralization, heparin binding, heparin neutralization or antimicrobial activity.

BPI protein products are described to have a variety of antimicrobial activities. For example, BPI protein products are bactericidal for gram-negative bacteria, as described in U.S. Pat. Nos. 5,198,541, 5,641,874, 5,948,408, 5,980,897 and 5,523,288. International Publication No. WO 94/20130 proposes methods for treating subjects suffering from an infection (e.g. gastrointestinal) with a species from the gram-negative bacterial genus Helicobacter with BPI protein products. BPI protein products also enhance the effectiveness of antibiotic therapy in gram-negative bacterial infections, as described in U.S. Pat. Nos. 5,948,408, 5,980,897 and 5,523,288 and International Publication Nos. WO 89/01486 (PCT/US99/02700) and WO 95/08344 (PCT/US94/11255). BPI protein products are also bactericidal for gram-positive bacteria and mycoplasma, and enhance the effectiveness of antibiotics in gram-positive bacterial infections, as described in U.S. Pat. Nos. 5,578,572 and 5,783,561 and International Publication No. WO 95/19180 (PCT/US95/00656). BPI protein products exhibit antifungal activity, and enhance the activity of other antifungal agents, as described in U.S. Pat. No. 5,627,153 and International Publication No. WO 95/19179 (PCT/US95/00498), and further as described for BPI-derived peptides in U.S. Pat. No. 5,858,974, which is in turn a continuation-in-part of U.S. application Ser. No. 08/504,841 and corresponding International Publication Nos. WO 96/08509 (PCT/US95/09262) and WO 97/04008 (PCT/US96/03845), as well as in U.S. Pat. Nos. 5,733,872, 5,763,567, 5,652,332, 5,856,438 and corresponding International Publication Nos. WO 94/20532 (PCT/US94/02465) and WO 95/19372 (PCT/US94/10427). BPI protein products exhibit anti-protozoan activity, as described in U.S. Pat. Nos. 5,646,114 and . 6,013,629 and International Publication No. WO 96/01647 (PCT/US95/08624). BPI protein products exhibit anti-chlamydial activity, as described in co-owned U.S. Pat. No. 5,888,973 and WO 98/06415 (PCT/US97/13810). Finally, BPI protein products exhibit anti-mycobacterial activity, as described in co-owned, co-pending U.S. application Ser. No. 08/626,646, which is in turn a continuation of U.S. application Ser. No.08/285,803, which is in turn a continuation-in-part of U.S. application Ser. No.08/031,145 and corresponding International Publication No. WO 94/20129 (PCT/US94/02463).

Of interest to the background of the present invention are metabolic oxidation-reduction indicator dyes, which measure electron transport activity. For example, Alamar Blue™, a tetrazolium based dye, is an oxidation-reduction indicator that both fluoresces and changes color in response to chemical reduction resulting from cell growth.

There continues to exist a need for novel antimicrobial agents useful for treating a variety of infections and for methods of identifying such novel compounds. Such methods ideally would provide for rapid and highly selective identification of compounds that may be structurally distinct from the major conventional antimicrobial agents.

SUMMARY OF THE INVENTION

The present invention generally provides methods for identifying antimicrobial compounds (including, for example, antifungal or antibacterial compounds) based on the discovery that a class of antimicrobial agents based on or derived from bactericidal/permeability-increasing protein (BPI) generates unique effects on fungal and bacterial cells as revealed by treatment with a metabolic oxidation-reduction indicator dye, Alamar Blue™. When BPI-derived peptide compounds are employed as antifungal agents, their effects are characterized by an unexpected apparent increase in metabolic oxidation-reduction activity before or concurrently with an onset of loss or reduction of fungal cell viability at the same peptide concentration. Similarly, when rBPI$_{21}$ or BPI-derived peptide compounds are employed as antibacterial agents, their effects are also characterized by an apparent increase in metabolic oxidation-reduction activity before or concurrently with an onset of loss or reduction of bacterial viability at the same peptide concentration.

Novel antimicrobial agents may be rapidly and selectively identified by screening candidate test compounds for replication of the characteristic apparent increase in target cell metabolic oxidation-reduction activity (relative to untreated control cells) that is produced by BPI protein products before or concurrently with the onset of loss (including reduction) of viability at the same candidate compound concentration within the tested target cell population. Sources of test compounds include, for example, libraries (including combinatorial libraries) of inorganic or organic compounds (for example, bacterial, fungal, mammalian, insect or plant products, peptides, peptidomimetics and/or organomimetics). Presently preferred standard BPI-derived peptides that are known to produce this characteristic pattern include XMP.391 (SEQ ID NO: 4) or XMP.445 (SEQ ID NO: 6).

This aspect of the invention thus contemplates a method of identifying a potential antimicrobial agent, particularly an antifungal compound, comprising the steps of: (a) contacting a target cell (e.g., a fungal cell or a bacterial cell) with a metabolic oxidation-reduction indicator dye in the presence and absence of test compound, and (b) detecting apparent increased metabolic activity in the presence of the test compound relative to metabolic activity in the absence of the test compound, before or concurrently with onset of loss or reduction of target cell viability at the same candidate compound concentration within the tested target cell population, or despite eventual loss or reduction of target cell viability. Compounds that provide this fingerprint are then selected as potential antimicrobial compounds and may undergo further testing. Any metabolic oxidation-reduction indicator dye capable of detecting metabolic activity, including mitochondrial metabolic activity, may be used; a presently preferred metabolic oxidation-reduction indicator dye is Alamar Blue™ [AccuMed Int'l, Westlake, Ohio]. The eventual loss or reduction of target cell viability may be confirmed by routine culture, through use of other dyes such as propidium iodide or trypan blue, or through the metabolic oxidation-reduction indicator dye itself by monitoring dye signal over time (wherein a lack of change in dye signal indicates that the cells have died).

It is further contemplated that screening methods according to the present invention may involve multiple further stages of screening, including selection of test compounds that have a differential effect on target cells in comparison to non-target cells (e.g., a reduced effect on mammalian cells relative to fungal or bacterial cells, or a greater effect on fungal cells relative to bacterial cells or vice versa). This aspect of the invention provides a further screening assay involving (a) contacting a mammalian cell with the metabolic oxidation-reduction indicator dye in the presence and absence of the test compound, and (b) observing the difference in dye signal between cells treated with the test compound and untreated control cells. Test compounds may be alternatively or additionally assayed for ability to kill or inhibit growth of target cells (e.g., fungal cells or bacteria) in vitro using any assays known in the art, including broth or radial diffusion assays, and for toxicity to mammalian cells using any assays known in the art. Suitable compounds may have a 2-fold, 10-fold, 50-fold, 100-fold, or greater separation (selectivity) between antimicrobial activity and mammalian cell activity. Optionally, the in vivo antimicrobial activity of test compounds may also be assayed in any animal models of infection known to those skilled in the art. Such assays include those for in vitro or in vivo oral availability or those for in vivo oral activity as evidenced by activity when administered orally in a comparative survival study.

Another aspect of the invention provides kits for use in conducting the screening methods of the present invention. Such kits may optionally include (a) a metabolic oxidation-reduction indicator dye and (b) a BPI-derived antimicrobial peptide or other BPI protein product suitable for use as a standard (positive control) against which the test compound may be compared.

Other agents that do not exhibit the characteristic "fingerprint," such as amphotericin B, fluconazole, itraconazole or antimycin (for fungal cells) or ciprofloxacin, tetracycline or polymyxin (for bacteria), may be used as an optional negative control.

The present invention also provides novel antimicrobial compounds identified by the screening methods of the present invention.

Yet a further aspect of the invention contemplates the treatment of infections, including fungal or bacterial infections, using compounds identified by the screening methods of the present invention that exhibit the above-described characteristic pattern, other than compounds known in the art (including BPI protein products such as BPI-derived peptides previously known in the art).

Numerous additional aspects and advantages of the invention will become apparent to those skilled in the art upon consideration of the following detailed description of the invention which describes presently prepared embodiments thereof.

DETAILED DESCRIPTION OF THE INVENTION

Figure 1:
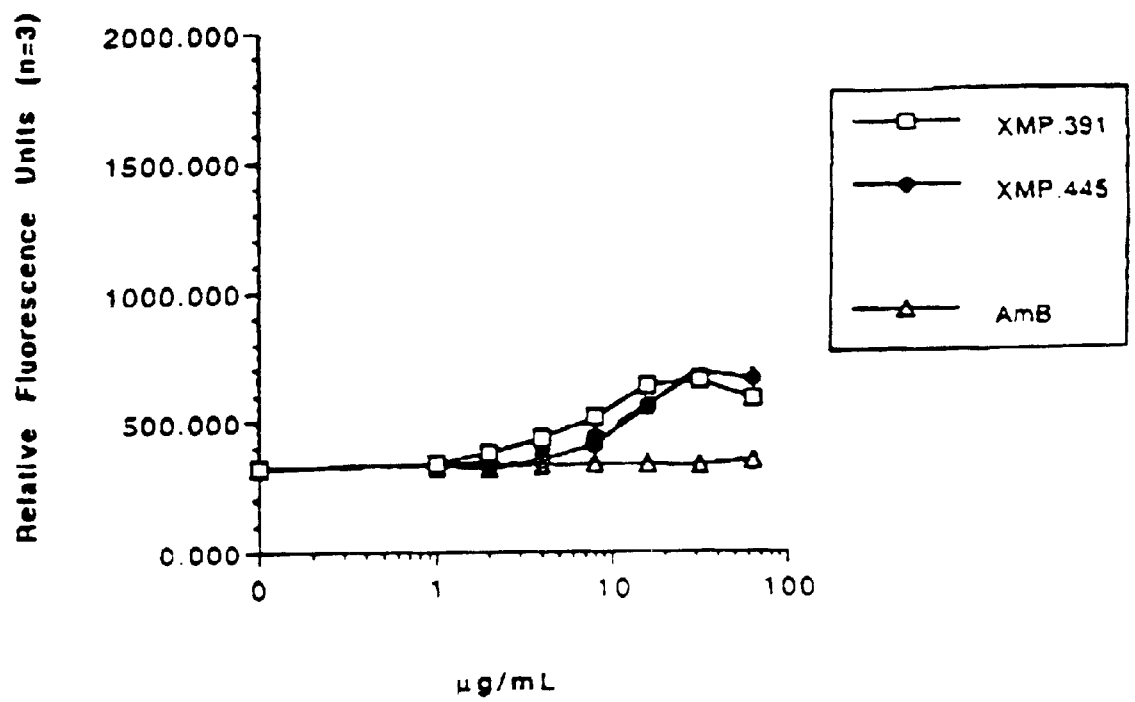
FIGS. 1, 2, 3 and 4 depict the effect of XMP.391 (SEQ ID NO: 4) and XMP.445 (SEQ ID NO: 6) on fungal cells treated with Alamar Blue™ at 0, 15, 30 and 45 minutes in a fluorimetric assay.

The present invention generally provides methods for identifying antimicrobial compounds that mimic the unique effects of BPI protein products, particularly BPI-derived antimicrobial peptides, on cells treated with a metabolic oxidation-reduction indicator dye, preferably a dye that detects mitochondrial or bacterial metabolic activity. This unique "fingerprint" manifests as an apparent increase in metabolic oxidation-reduction activity (as measured, for example, by an increased dye fluorescence intensity) before or concurrently with onset of loss or reduction of target cell viability. This apparent increase in metabolic activity relative to untreated control cells is best observed at an antimicrobial peptide concentration that is less than the minimum microbicidal concentration and at certain time points, depending on how the assay is performed. Exemplary assays and conditions are described in the Examples herein, and sample characteristic fingerprints are illustrated in the Figures herein.

The invention is based on the discovery that antimicrobial agents based on or derived from bactericidal/permeability-increasing protein (BPI) display unexpectedly unique effects on fungal cells and bacteria treated with a metabolic oxidation-reduction indicator dye, such as Alamar Blue™. A characteristic pattern of an apparent increase in metabolic activity (as measured, for example, by an increased dye fluorescence intensity), before or concurrently with onset of loss or reduction of target cell viability, at one or more antimicrobial peptide concentrations less than the minimum microbicidal concentration provides an unexpected "fingerprint" because dying or dead target cells would not be expected to have a higher metabolic activity than healthy, untreated target cells.

Any metabolic oxidation-reduction indicator dyes that are capable of detecting mitochondrial metabolic activity and provide the above-described unique "fingerprint" of BPI protein products may be used in the methods or kits of the present invention. For example, the Sigma [St. Louis, Mo.] catalog lists metabolic indicator dyes that include a number of tetrazolium based dyes. Presently preferred is the tetrazolium based dye Alamar Blue™ [AccuMed Int'l, Westlake, Ohio].

Any BPI protein product which displays the above-described characteristic pattern of increased metabolic activity may be used as a standard against which the test compound may be compared. Presently preferred are $rBPI_{21}$ or BPI-derived peptides, including domain III-derived peptides such as XMP.391 (SEQ TD NO: 4) [the structure of which is described in Table 1 of U.S. Pat. No. 5,858,974 and corresponding International Publication No. WO 97/04008 (PCT/US96/03845), both of which are incorporated by reference herein] or XMP.445 (SEQ ID NO: 6) [the structure of which is described in co-owned, U.S. Provisional Application Serial No. 60/101,958 filed Sep. 25, 1998 and No. 60/109,896 filed Nov. 25, 1998, both of which are incorporated by reference herein]. Procedures for the preparation and purification of BPI-derived peptides are described in, for example, U.S. Pat. Nos. 5,858,974, 5,733,872 and 5,652,332, incorporated herein by reference.

Test compounds may be assayed on any organism, including those involved in pathogenic infection. Fungal species include, e.g., Candida (including *C. albicans, C tropicalis, C. parapsilosis, C. stellatoidea, C. krusei, C. parakrusei, C. lusitanae, C. pseudotropicalis, C. guilliermondi* or *C. glabrata*), Aspergillus (including *A. fumnigatus, A. flavus, A. niger, A. nidulans, A. terreus, A. sydowi, A. flavatus,* or *A. glaucus*), Cryptococcus, Histoplasma, Coccidioides, Paracoccidioides, Blastomyces, Basidiobolus, Conidiobolus, Rhizopus, Rhizomucor, Mucor, Absidia, Mortierella, Cunninghamella, Saksenaea, Pseudallescheria, Sporotrichosis, Fusarium, Trichopkyton, Trichosporon, Microsporum, Epidemiophyton, Scytalidium, Malassezia, Actinomycetes, Sporothrix, Penicillium, Saccharomyces or Pneumocystis.

Gram-negative bacterial species that may be tested include Acidaminococcus, Acinetobacter, Aeromonas, Alcaligenes, Bacteroides, Bordetella, Branhamella, Brucella, Calymmatobacterium, Campylobacter, Cardiobacterium, Chrornobacterium, Citrobacter, Edwardsiella, Enterobacter, Escherichia, Flavobacterium, Francisella, Fusobacterium, Haemophilus, Klebsiella, Legionella, Moraxella, Morganella, Neisseria, Pasturella, Plesiomonas, Porphyromonas, Prevotella, Proteus, Providencia, Pseudomonas, Salmonella, Serratia, Shigella, Streptobacillus, Treponema, Veillonella, Vibrio, or Yersinia species as well as Chlamnydia; while gram-positive bacterial species that may be tested include Staphylococcus, Streptococcus, Micrococcus, Peptococcus, Peptostreptococcus, Enterococcus, Bacillus, Clostridium, Lactobacillus, Listeria, Erysipelothrix, Propionibacterium, Eubacterium, or Corynebacterium species as well as Mycoplasma, Ureaplasma, or Mycobacteria.

Protozoa include Plasmodia, Toxoplasma, Leishmania, Trypanosoma. Giadia, Entamoeba, Acanthacmoeba, Nagleria, Hartmanella, Balantiditum, Babesia, Cryptosporidium, Isospora, Microsporidium, Trichomonas or Pneunocystis species; other parasites include helminths.

Sources for test compounds to be screened include (1) inorganic or organic chemical libraries, (2) natural product libraries, or (3) combinatorial libraries comprised of either random or mimetic peptides, oligonucleotides or organic molecules. Chemical libraries may be readily synthesized or purchased from a number of commercial sources, and may include structural analogs of known compounds or compounds that are identified as "hits" or "leads" via natural product screening. The sources of natural product libraries are collections of microorganisms (including bacteria or fungi), animals, plants or other vegetation, or marine organisms, and libraries of mixtures for screening may be created by: (1) fermentation and extraction of broths from soil, plant or marine microorganisms or (2) extraction of the organisms themselves. Natural product libraries include polyketides, non-ribosomal peptides, and/or variants (non-naturally occurring) variants thereof. For a review, see *Science* 282:63–68 (1998). Combinatorial libraries are composed of large numbers of peptides, oligonucleotides or organic compounds and can be readily prepared by traditional automated synthesis methods, PCR, cloning or proprietary synthetic methods. Of particular interest are peptide or oligonucleotide combinatorial libraries. Still other libraries of interest include peptide, protein, peptidomimetic, multiparallel synthetic collection, recombinatorial, or polypeptide libraries. For a review of combinatorial chemistry and libraries created therefrom, see Myers, *Curr. Opin. Biotechnol.* 8:701–707 (1997). For reviews and examples of peptidomimetic libraries, see Al-Obeidi et al., *Mol. Biotechnol,* 9(3):205–23 (1 998); Hruby et al., *Curr Opin Chem Biol,* 1(1): 14–19 (1997); Domer et al., *Bioorg Med Chem,* 4(5):709–15 (1996) (alkylated dipeptides). A variety of companies have constructed chemical libraries and provide their use for screening, including for example, 3-Dimensional Pharmaceuticals, Exton, Pa.; Agouron Pharmaceutical, La Jolla, Calif.; Alanex Corp., San Diego, Calif.; Ariad Pharmaceuticals, Cambridge, Mass.; ArQule, Inc., Medford, Mass.; Arris Pharmaceutical, S. San Francisco, Calif.; Axys, S. San Francisco, Calif.: Biocryst Pharmaceuticals, Birmingham, Ala.; Cadus Pharmaceuticals, Tarrytown, N.Y.; Cambridge Combinatorial, Cambridge, UK; ChemGenics, Cambridge, Mass.; CombiChem, San Diego, Calif., Corvas International, San Dicgo, Calif.; Cubist Pharmaceuticals, Cambridge, Mass.; Darwin Molecular, Bothell, Wash.; Houghten Pharmaceuticals, San Diego, Calif., Hybridon. Cambridge, Mass.; Isis Pharmaceuticals, Carlsbad, Calif; Ixsys, San Diego, Calif.; Molecumctics, Bellevue, Wash.; Peptide Therapeutics, Cambridge, UK; Pharmacopia, Princeton, N.J.; SUGEN, Redwood City, Calif.; Telik, Inc., S. San Francisco, Calif.; or Tripos, Inc., St. Louis, Mo..

Preferably the compounds that are preliminarily identified by this method are then assayed by conventional methods known in the art for the ability to kill or inhibit growth/replication of whole target cells in vitro. Such assays may include the steps of contacting test compounds with whole target cells and measuring viability or proliferation of the target cells. Any assays known in the art may be used, including those described in Examples 2 and 3 of U.S. Pat. No. 5,858,974.

Some compounds may be more suitable for in vitro use, including, for example, use as a preservative or decontaminant for fluids or surfaces, or use to sterilize surgical or other medical equipment or implantable devices, either ex vivo or in situ, including prosthetic joints or indwelling invasive devices such as intravenous lines or catheters which are often foci of infection, or use in the preparation of growth media for non-target cells.

Ideally, the most desirable compounds for in vivo administration to mammals will have a differential effect on target and mammalian cells, i.e., if the compound does adversely affect mammalian cells, a higher concentration of the compound would be required to affect the mammalian cells in comparison to target cells, thereby providing a therapeutic window of suitable concentrations for administering the compound without undesirable toxic effects. The relative effect on target and mammalian cells may be determined using any in vitro assays known in the art, including by contacting mammalian cells with the same metabolic oxidation-reduction indicator dye utilized for the initial antimicrobial screen, or a different dye, in the presence and absence of the same test compound, detecting dye signal, and selecting compounds that do not produce a substantial difference in dye signal between the treated cells and untreated control cells.

The growth inhibitory (or toxic) effect of test compounds on mammalian cells may be determined through their effect on proliferation, viability or metabolic activity of mammalian cells, using any methods known in the art, e.g., by measuring uptake of tritiated amino acids or nucleotides, by using viability dyes such as propidium iodide or trypan blue; or by using metabolic dyes such as Alamar Blue™ or membrane potential indicator dyes such as such as $DiOC_6$(3), JC-1, rhodamine 123, or MitoTracker® reduced dyes.

Additionally assays may be performed to evaluate in vitro or in vivo oral availability of the test compound or in vivo oral activity of the test compound as evidenced by activity when administered orally in a comparative survival study. Assays for oral availability are described in co-owned U.S. Provisional Application Serial No.60/143,485 filed July 12, 1999 and corresponding U.S. application Ser. No. 09/404, 926 filed Sep. 24, 1999 and International Application No. PCT/US99/22361 filed Sep. 24, 1999, all of which are incorporated herein by reference.

The potential antimicrobial compounds may also be evaluated for their effect in any model of infection, including any in vivo model, known in the art. Exemplary animal models of fungal infection are described in Example 4 of U.S. Pat. No. 5,858,974, incorporated herein by reference, and may be modified for any fungal species (including Candida, Aspergillus or Fusarium). Exemplary animal models of bacterial infection are described in U.S. Pat. Nos. 5,523,288 and 5,578,572, incorporated herein by reference, and may be modified for any bacterial species. Exemplary animal models of protozoan infection include those described in U.S. Pat. No. 5,646,114, incorporated herein by reference. Other microbial infection models are known in the art. The most desirable compounds are capable of preventing the establishment of an infection or reversing the outcome of an infection once it is established without excessive toxicity.

The use of antimicrobial compounds identified by the screening methods of the present invention is contemplated for the treatment of subjects suffering from microbial infection, especially mammalian subjects such as humans, but also including farm animals such as cows, sheep, pigs, horses, goats or poultry (e.g., chickens, turkeys, ducks or geese), companion animals such as dogs or cats, exotic and/or zoo animals, or laboratory animals including mice, rats, rabbits, guinea pigs, or hamsters. Treatment of infection of plants is also contemplated. "Treatment" as used herein encompasses both prophylactic and/or therapeutic treatment, and may be accompanied by concurrent administration of other antimicrobial agent(s), including any of the agents discussed herein.

Therapeutic compositions may be administered systemically or topically. Systemic routes of administration include oral, intravenous, intramuscular or subcutaneous injection (including into a depot for long-term release), intraocular or retrobulbar, intrathecal, intraperitoneal (e.g. by intraperitoneal lavage), intrapulmonary (using powdered drug, or an aerosolized or nebulized drug solution), or transdermal. Suitable dosages include doses ranging from 1 µg/kg to 100 mg/kg per day or doses ranging from 0.1 mg/kg to 20 mg/kg per day.

Topical routes include administration in the form of salves, creams, jellies, ophthalmic drops or ointments (as described in co-owned, co-pending U.S. application Ser. Nos. 08/557,289 and 08/557,287, both filed Nov. 14, 1995), ear drops, suppositories, irrigation fluids (for, e.g., irrigation of wounds) or medicated shampoos. For example, for topical administration in drop form, about 10 to 200 µL of a therapeutic composition may be applied one or more times per day as determined by the treating physician.

For polypeptide therapeutics that are amenable to administration via gene therapy, methods of delivering suitable genes to a subject (including plants or animals) are contemplated.

Those skilled in the art can readily optimize effective dosages and administration regimens for therapeutic compositions as determined by good medical practice and the clinical condition of the individual subject.

"Concurrent administration," or "co-administration," as used herein includes administration of one or more agents, in conjunction or combination, together, or before or after each other. The agents may be administered by the same or by different routes. If administered via the same route, the agents may be given simultaneously or sequentially, as long as they are given in a manner sufficient to allow all agents to achieve effective concentrations at the site of action.

Known antifungal agents include polyene derivatives, such as amphotericin B (including lipid or liposomal formulations thereof) or the structurally related compounds nystatin or pimaricin; flucytosine (5-fluorocytosine); azole derivatives (including ketoconazole, clotrimazole, miconazole, econazole, butoconazole, oxiconazole, sulconazole, tioconazole, terconazole, fluconazole, itraconazole, voriconazole [Pfizer], poscaconazole [SCH56592, Schering-Plough]) or ravuconazole; allylamines-thiocarbamates (including tolnaftate, naftifine or terbinafine); griseofulvin; ciclopirox; haloprogin; echinocandins (including caspofungin [MK-099 1, Merck], FK463 [Fujisawa], or VER-002 [Versicor]); nikkomycins; or sordarins. Recently discovered as antifungal agents are a class of products related to bactericidal/permeability-increasing protein (BPI), described in U.S. Pat. Nos. 5,627, 153, 5,858,974, 5,652,332, 5,856,438, 5,763,567 and 5,733, 872, the disclosures of all of which are incorporated herein by reference.

The polyene derivatives, which include amphotericin B or the structurally related compounds nystatin or pimaricin, are broad-spectrum antifungals that bind to ergosterol, a component of fungal cell membranes, and thereby disrupt the membranes. Amphotericin B is usually effective for systemic mycoses, but its administration is limited by toxic effects that include fever and kidney damage, and other accompanying side effects such as anemia, low blood pressure, headache, nausea, vomiting and phlebitis. The unrelated antifungal agent flucytosine (5-fluorocytosine), an orally absorbed drug, is frequently used as an adjunct to amphotericin B treatment for some forms of candidiasis and cryptococcal meningitis. Its adverse effects include bone marrow depression with leukopenia and thrombocytopenia.

The azole derivatives impair synthesis of ergosterol and lead to accumulation of metabolites that disrupt the function of fungal membrane-bound enzyme systems (e.g., cytochrome P450) and inhibit fungal growth. This group of agents includes ketoconazole, clotrimazole, miconazole, econazole, butoconazole, oxiconazole, sulconazole, tioconazole, terconazole, fluconazole or itraconazole. Significant inhibition of mammalian P450 results in significant drug interactions. Some of these agents may be administered to treat systemic mycoses. Ketoconazole, an orally administered imidazole, is used to treat nonmeningeal blastomycosis, histoplasmosis, coccidioidomycosis or paracoccidioidomycosis in non-immunocompromised patients, and is also useful for oral and esophageal candidiasis. Adverse effects include rare drug-induced hepatitis; ketoconazole is also contraindicated in pregnancy. Itraconazole appears to have fewer side effects than ketoconazole and is used for most of the same indications. Fluconazole also has fewer side effects than ketoconazole that is used for oral and esophageal candidiasis and cryptococcal meningitis. Miconazole is a parenteral imidazole with efficacy in coccidioldomycosis and several other mycoses, but has side effects including hyperlipidemia and hyponatremia.

The allylamines-thiocarbamates are generally used to treat skin infections. This group includes tolnaflate, naftifine or terbinafine. Another antifungal agent is griseofulvin, a fungistatic agent which is administered orally for fungal infections of skin, hair or nails that do not respond to topical treatment. Other topical agents include ciclopirox or haloprogin. Yet another topical agent is butenafine (Syed et al., *J. Dermatol.*, 25:648–652 (1988)). [Chapter 49 in Goodman and Gilman, *The Pharmacological Basis of Therapeutics*, 9th ed., McGraw-Hill, New York (1996), pages 1175–1190.]

BPI protein products, a class of products related to bactericidal/permeability-increasing protein (BPI), are described in U.S. Pat. No. 5,627,153 and corresponding International Publication No. WO 95/19179 (PCT/US95/00498), all of which are incorporated by reference herein, to have antifungal activity. BPI-derived peptides with antifungal activity are described in U.S. Pat. No. 5,858,974, which is in turn a continuation-in-part of U.S. application Ser. No. 08/504,841 filed Jul. 20, 1994 and corresponding International Publication Nos. WO 96/08509 (PCT/US95/09262) and WO 97/04008 (PCT/US96/03845), all of which are incorporated by reference herein. Other peptides with antifungal activity are described in U.S. Pat. Nos. 5,652,332 and 5,856,438 [corresponding to International Publication No. WO 95/19372 (PCT/US94/10427)], and in U.S. Pat. Nos. 5,763,567 and 5,733,872 [corresponding to International Publication No. WO 94/20532 (PCT/US94/02465)], which is a continuation-in-part of U.S. patent application Ser. No. 08/183,222 filed Jan. 14, 1994, which is a continuation-in-part of U.S. patent application Ser. No. 08/093,202 filed Jul. 15, 1993 [corresponding to International Publication No. WO 94/20128 (PCT/US94/0240 1)], which is a continuation-in-part of U.S. patent application Ser. No. 08/030,644 filed Mar. 12, 1993, now U.S. Pat. No. 5,348,942, the disclosures of all of which are incorporated herein by reference.

Known antibacterial agents include antibiotics, which are natural chemical substances of relatively low molecular weight produced by various species of microorganisms, such as bacteria (including Bacillus species), actinomycetes (including Streptomyces) or fungi, that inhibit growth of or destroy other microorganisms. Substances of similar structure and mode of action may be synthesized chemically, or natural compounds may be modified to produce semi-synthetic antibiotics. These biosynthetic and semi-synthetic derivatives are also effective as antibiotics. The major classes of antibiotics are (1) the β-lactams, including the penicillins, cephalosporins or monobactams; (2) the aminoglycosides, e.g., gentamicin, tobramycin, netilmycin, or amikacin; (3) the tetracyclines; (4) the sulfonamides and/or trimethoprim; (5) the fluoroquinolones, e.g., ciprofloxacin, norfloxacin, or ofloxacin; (6) vancomycin; (7) the macrolides, which include for example, erythromycin, azithromycin, or clarithromycin; and (8) other antibiotics, e.g., the polymyxins, chloramphenicol or the lincosamides.

Antibiotics accomplish their anti-bacterial effect through several mechanisms of action which can be generally grouped as follows: (1) agents acting on the bacterial cell wall such as bacitracin, the cephalosporins, cycloserine, fosfomycin, the penicillins, nistocetin, or vancomycin; (2) agents affecting the cell membrane or exerting a detergent effect, such as colistin, novobiocin or polymyxins; (3) agents affecting cellular mechanisms of replication, information transfer, and protein synthesis by their effects on ribosomes, e.g., the aminoglycosides, the tetracyclines, chloramphenicol, clindamycin, eyeloheximide, fucidin, lincomycin, puromycin, rifampicin, other streptomycins, or the macrolide antibiotics such as erythromycin or oleandomycin; (4) agents affecting nucleic acid metabolism, e.g., the fluoroquinolones, actinomycin, ethambutol, 5-fluorocytosine, griseofulvin, rifamycins; and (5) drugs affecting intermediary metabolism, such as the sulfonamides, trimethoprim, or the tuberculostatic agents isoniazid or para-aminosalicylic acid. Some agents may have more than one primary mechanism of action, especially at high concentrations. In addition, secondary changes in the structure or metabolism of the bacterial cell often occur after the primary effect of the antimicrobial drug.

The penicillins have a characteristic double-ring system composed of a β-lactam ring, which provides the antibacterial activity, and a thiazolidene ring. The penicillins are differentiated by a single side chain that is unique for each penicillin. The compounds are bactericidal and act by inhibiting bacterial transpeptidase, an enzyme involved in synthesis of the bacterial cell wall. Because of their mechanism of action, penicillins are generally active against growing, but not resting, cells. Penicillins, especially penicillin G, have largely gram-positive activity; the relative insensitivity of gram-negative rods to penicillin G and several other penicillins is probably due to the permeability barrier of the outer membrane of gram-negative bacteria. Ampicillin, carbenicillin, ticarcillin, and some other penicillins are active against gram-negative bacteria because they can pass through this outer membrane. Penicillins have relatively few adverse effects, the most important of which are the hypersensitivity (allergic) reactions. These compounds are widely distributed in the body, but do not enter cells and do not usually accumulate in CSF.

Bacterial resistance to the penicillins is by production of the enzyme β-lactamase, which catalyzes hydrolysis of the β-lactam ring. The percentage of bacteria resistant to penicillin has risen to about 80%. Several penicillins, including methicillin, oxacillin, cloxacillin, dicloxacillin or nafcillin, are not affected by the β-lactamase of staphylococci. These antibiotics are useful against most β-lactamase-producing species of Staphylococcus. However, a small number of species are resistant even to these penicillins. Some penicillins, amoxicillin and ticarcillin, are marketed in combination with clavulanic acid, which is a β-lactamase inhibitor that covalently binds to the enzyme and prevents it from hydrolyzing the antibiotics. Another inhibitor, sulbactam, is marketed in combination with ampicillin.

The cephalosporins are characterized by a β-lactam ring, like the penicillins, but have an adjacent dihydrothiazine ring instead of a thiazolidene ring. For convenience, these compounds are generally classified by generations. The first generation includes cephalothin, cephapirin, cefazolin, cephalexin, cephradine or cefadroxil. These drugs generally have excellent gram-positive activity except for enterococci and methicillin-resistant staphylococci, and have only modest gram-negative coverage. The second generation includes cefamandole, cefoxitin, ceforanide, cefuroxime, cefuroxime axetil, cefaclor, cefonicid or cefotetan. This veneration generally loses some gram-positive activity by weight and gains limited gram-negative coverage. The third generation includes cefotaxime, moxalactam, ceftizoxime, ceftriaxone, cefoperazone or ceftazidime. These compounds generally sacrifice further gram-positive activity by weight but gain substantial gram-negative coverage against Enterobacter and sometimes are active against Pseudomonas. The cephalosporins bind to penicillin-binding proteins with varying affinity. Once binding occurs, protein synthesis is inhibited. Cephalosporins are usually well tolerated; adverse effects include hypersensitivity reactions and gastrointestinal effects. Cephalosporins may interact with nephrotoxic drugs, particularly aminoglycosides, to increase toxicity. Resistance to cephalosporins is mediated by several mechanisms, including production of β-lactamase, although some strains that do not produce β-lactamase are nevertheless resistant.

Imipenem is a N-formimidoyl derivative of the mold product thienamycin. It contains a β-lactam ring and somewhat resembles penicillin except for differences in the second ring. It has activity against both gram-positive and gram-negative organisms and is resistant to most β-lactamases, although not those from Pseudomonas. It is marketed in combination with cilastin, a compound that inhibits inactivation of imipenem in the kidney by renal dihydropeptidase I enzyme. Cilastin increases the concentration of imipenem in urine, although not in blood.

Aztreonam is the first of a new group of antibiotics referred to as the monobactams. These agents have a β-lactam ring but lack the second ring characteristic of the penicillins and cephalosporins. It acts by binding to penicillin-binding proteins, and produces long, filamentous bacterial shapes that eventually lyse. Aztreonam is active only against aerobic gram-negative bacteria, is susceptible to inactivation by some β-lactamases, and has few adverse effects.

The aminoglycosides contain amino sugars linked to an aminocyclitol ring by glycosidic bonds. They have similar mechanisms of action and properties, but differ somewhat in spectrum of action, toxicity, and susceptibility to bacterial resistance. The compounds are bactericidal, with activity against both gram-positive and gram-negative organisms, and act by binding to proteins on the 30S ribosome of bacteria and inhibiting protein synthesis. The aminoglycosides also bind to isolated LPS and have a very weak outer membrane permeabilizing effect. [Taber et al., *Microbiological Reviews* 53: 439–457 (1987)); Kadurugamuwa et al., *Antimicrobial Agents and Chemotherapy*, 37: 715–721 (1993); Vaara, *Microbiological Reviews* 56: 395–411 (1992)]. This class of antibiotics includes amikacin, gentamicin, kanamycin, neomycin, netilmycin, paromomycin or tobramycin. The aminoglycosides are usually reserved for more serious infections because of severe adverse effects including ototoxicity and nephrotoxicity. There is a narrow therapeutic window between the concentration required to produce a therapeutic effect, e.g., 8 μg/ml for gentamicin, and the concentration that produces a toxic effect, e.g., 12 μg/ml for gentamicin. Neomycin in particular is highly toxic and is never administered parenterally.

Tetracyclines have a common four-ring structure and are closely congeneric derivatives of the polycyclic naphthacenecarboxamide. The compounds are bacteriostatic, and inhibit protein synthesis by binding to the 30S subunit of microbial ribosomes and interfering with attachment of aminoacyl tRNA. The compounds have some activity against both gram-positive and gram-negative bacteria; however, their use is limited because many species are now relatively resistant. Adverse effects include gastrointestinal effects, hepatotoxicity with large doses, and nephrotoxicity in some patients. This antibiotic class includes tetracycline, chlortetracycline, demeclocycline, doxycycline, methacycline, minocycline or oxytetracycline.

The sulfonamides are derivatives of sulfanilamide, a compound similar in structure to para-aminobenzoic acid (PABA), which is an essential precursor for bacterial synthesis of folic acid. The compounds are generally bacteriostatic, and act by competitively inhibiting incorporation of PABA into tetrahydrofolic acid, which is a required cofactor in the synthesis of thymidines, purines and DNA. Sulfonamides have a wide range of activity against gram-positive and gram-negative bacteria, but their usefulness has diminished with increasingly high prevalence of bacterial resistance. The sulfonamide class of antibiotics includes sulfacytine, sulfadiazine, sulfamethizole, sulfisoxazole, sulfamethoxazole, sulfabenzamide or sulfacetamide. Adverse effects include hypersensitivity reactions and occasional hematological toxicity.

Trimethoprim is an inhibitor of the dihydrofolate reductase enzyme, which converts dihydrofolic to tetrahydrofolic acid, a required factor for DNA synthesis. Adverse effects include gastrointestinal distress and rare hematological toxicity. Trimethoprim is also available in combination with sulfamethoxazole (also known as co-trimoxazole). The combination is usually bactericidal, although each agent singly is usually bacteriostatic. The combination is the drug of choice for Salmonella infections, some Shigella infections, *E. coli* traveler's diarrhea and Pneumocystis carinii pneumonia.

The fluoroquinolones and quinolones are derivatives of nalidixic acid, a naphthyridine derivative. These compounds are bactericidal, and impair DNA replication, transcription and repair by binding to the DNA and interfering with DNA gyrase, an enzyme which catalyzes negative supercoiling of DNA. The fluoroquinolones, which include norfloxacin, ciprofloxacin, or ofloxacin, and the quinolones, which include cinoxacin, have a broad spectrum of antimicrobial activity against gram-negative and gram-positive organisms. These compounds distribute widely through extravascular tissue sites, have a long serum half-life, and present few adverse effects. Because of their effect on DNA, the drugs are contraindicated in pregnant patients and in children whose skeletal growth is incomplete.

Vancomycin is a glycopeptide, with a molecular weight of about 1500, produced by a fungus. It is primarily active against gram-positive bacteria. The drug inhibits one of the final steps in synthesis of the bacterial cell wall, and is thus effective only against growing organisms. It is used to treat serious infections due to gram-positive cocci when penicillin G is not useful because of bacterial resistance or patient allergies. Vancomycin has two major adverse effects, ototoxicity and nephrotoxicity. These toxicities can be potentiated by concurrent administration of another drug with the same adverse effect, such as an aminoglycoside.

The macrolides are bacteriostatic and act by binding to the 50S subunit of 70S ribosomes, resulting in inhibition of protein synthesis. They have a broad spectrum of activity against gram-positive and gram-negative bacteria and may be bacteriostatic or bactericidal, depending on the concentration achieved at sites of infection. The compounds distribute widely in body fluids. Adverse effects include gastrointestinal distress and rare hypersensitivity reactions. The most common macrolide used is erythromycin, but the class includes other compounds such as clarithromycin or azithromycin.

The polymyxins are a group of closely related antibiotic substances produced by strains of *Bacillus polymyxa*. These drugs, which are cationic detergents, are relatively simple, basic peptides with molecular weights of about 1000. Their antimicrobial activity is restricted to gram-negative bacteria. They interact strongly with phospholipids and act by penetrating into and disrupting the structure of cell membranes. Polymyxin B also binds to the lipid A portion of endotoxin and neutralizes the toxic effects of this molecule. Polymyxin B has severe adverse effects, including nephrotoxicity and neurotoxicity, and should not be administered concurrently with other nephrotoxic or neurotoxic drugs. The drug thus has limited use as a therapeutic agent because of high systemic toxicity, but may be used for severe infections, such as *Pseudomonas aeruginosa* meningitis, that respond poorly to other antibiotics.

Chloramphenicol inhibits protein synthesis by binding to the 50S ribosomal subunit and preventing binding of aminoacyl tRNA. It has a fairly wide spectrum of antimicrobial activity, but is only reserved for serious infections, such as meningitis, typhus, typhoid fever, and Rocky Mountain spotted fever, because of its severe and fatal adverse hematological effects. It is primarily bacteriostatic, although it may be bactericidal to certain species.

Lincomycin and clindamycin are lincosamide antimicrobials. They consist of an amino acid linked to an amino sugar. Both inhibit protein synthesis by binding to the 50S ribosomal subunit. They compete with erythromycin and chloramphenicol for the same binding site but in an overlapping fashion. They may be bacteriostatic or bactericidal, depending on relative concentration and susceptibility. Gastrointestinal distress is the most common side effect. Other adverse reactions include cutaneous hypersensitivity, transient hematological abnormalities, and minor elevations of hepatic enzymes. Clindamycin is often the drug of choice for infections caused by anaerobic bacteria or mixed aerobic/anaerobic infections, and can also be used for susceptible aerobic gram-positive cocci.

Some drugs, e.g. aminoglycosides, have a small therapeutic window. For example, 2 to 4 $\mu$g/ml of gentamicin or tobramycin may be required for inhibition of bacterial growth, but peak concentrations in plasma above 6 to 10 $\mu$g/ml may result in ototoxicity or nephrotoxicity. These agents are more difficult to administer because the ratio of toxic to therapeutic concentrations is very low. Antimicrobial agents that have toxic effects on the kidneys and that are also eliminated primarily by the kidneys, such as the aminoglycosides or vancomycin, require particular caution because reduced elimination can lead to increased plasma concentrations, which in turn may cause increased toxicity. Doses of antimicrobial agents that are eliminated by the kidneys must be reduced in patients with impaired renal function. Similarly, dosages of drugs that are metabolized or excreted by the liver, such as erythromycin, chloramphenicol, or clindamycin, must be reduced in patients with decreased hepatic function.

Bacteria acquire resistance to antibiotics through several mechanisms: (1) production of enzymes that destroy or inactivate the antibiotic [Davies, *Science*, 264:375–381 (1994)]; (2) synthesis of new or altered target sites on or within the cell that are not recognized by the antibiotic [Spratt, *Science*, 264:388–393 (1994)]; (3) low penmeability to antibiotics, which can be reduced even further by altering cell wall proteins, thus restricting access of antibiotics to the bacterial cytoplasmic machinery; (4) reduced intracellular transport of the drug; and (5) increased removal of antibiotics from the cell via membrane-associated pumps [Nikaido, *Science*, 264:382–387 (1994)].

The susceptibility of a bacterial species to an antibiotic is generally determined by any art recognized microbiological method. A rapid but crude procedure uses commercially available filter paper disks that have been impregnated with a specific quantity of the antibiotic drug. These disks are placed on the surface of agar plates that have been streaked with a culture of the organism being tested, and the plates are observed for zones of growth inhibition. A more accurate technique, the broth dilution susceptibility test, involves preparing test tubes containing serial dilutions of the drug in liquid culture media, then inoculating the organism being tested into the tubes. The lowest concentration of drug that inhibits growth of the bacteria after a suitable period of incubation is reported as the minimum inhibitory concentration.

The resistance or susceptibility of an organism to an antibiotic is determined on the basis of clinical outcome, i.e., whether administration of that antibiotic to a subject infected by that organism will successfully cure the subject. While an organism may literally be susceptible to a high concentration of an antibiotic in vitro, the organism may in fact be resistant to that antibiotic at physiologically realistic concentrations. It the concentration of drug required to inhibit growth of or kill the organism is greater than the concentration that can safely be achieved without toxicity to the subject, the microorganism is considered to be resistant to the antibiotic. To facilitate the identification of antibiotic resistance or susceptibility using in vitro test results, the National Committee for Clinical Laboratory Standards (NCCLS) has formulated standards for antibiotic susceptibility that correlate clinical outcome to in vitro determinations of the minimum inhibitory concentration of antibiotic.

As used herein, "BPI protein product" includes naturally or recombinantly produced BPI protein; natural, synthetic, or recombinant biologically active polypeptide fragments of BPI protein; biologically active polypeptide variants of BPI protein or fragments thereof, including hybrid fusion proteins or dimers; biologically active polypeptide analogs of BPI protein or fragments or variants thereof, including cysteine-substituted analogs; or BPI-derived peptides. The BPI protein products administered according to this invention may be generated and/or isolated by any means known in the art. U.S. Pat. Nos. 5,198,541 and 5,641,874, the disclosures of which are incorporated herein by reference, disclose recombinant genes encoding, and methods for expression of, BPI proteins including recombinant BPI holoprotein, referred to as rBPI and recombinant fragments of BPI. U.S. Pat. No. 5,439,807 and corresponding International Publication No. WO 93/23540 (PCT/US93/04752), which are all incorporated herein by reference, disclose novel methods for the purification of recombinant BPI protein products expressed in and secreted from genetically transformed mammalian host cells in culture and discloses how one may produce large quantities of recombinant BPI products suitable for incorporation into stable, homogeneous pharmaceutical preparations.

Biologically active fragments of BPI (BPI fragments) include biologically active molecules that have the same or similar amino acid sequence as a natural human BPI holoprotein, except that the fragment molecule lacks amino-terminal amino acids, internal amino acids, and/or carboxy-terminal amino acids of the holoprotein, including those described in U.S. Pat. Nos. 5,198,541 and 5,641,874. Non-limiting examples of such fragments include an N-terminal fragment of natural human BPI of approximately 25 kD, described in Ooi et al., *J. Exp. Med.*, 174:649 (1991), or the recombinant expression product of DNA encoding N-terminal amino acids from 1 to about 193 to 199 of natural human BPI, described in Gazzano-Santoro et al., *Infect. Immmun.* 60:4754–4761 (1992), and referred to as rBPI$_{23}$. In that publication, an expression vector was used as a source of DNA encoding a recombinant expression product (rBPI$_{23}$) having the 31-residue signal sequence and the first 199 amino acids of the N-terminus of the mature human BPI, as set out in FIG. 1 of Gray et al., supra, except that valine at position 151 is specified by GTG rather than GTC and residue 185 is glutamic acid (specified by GAG) rather than lysine (specified by AAG). Recombinant holoprotein (rBPI) has also been produced having the sequence (SEQ ID NOS: 1 and 2) set out in FIG. 1 of Gray et al., supra, with the exceptions noted for rBPI$_{23}$ and with the exception that residue 417 is alanine (specified by GCT) rather than valine (specified by GTT). Another fragment consisting of residues 10–193 of BPI has been described in U.S. Pat. No. 6,013,631, continuation-in-part U.S. application Ser. No. 09/336,402, filed Jun. 18, 1999, and corresponding International Publication No. WO 99/66044 (PCT/US99/13860), all of which are incorporated herein by reference. Other examples include dimeric forms of BPI fragments, as described in U.S. Pat. Nos. 5,447,913, 5,703,038, and 5,856,302 and corresponding International Publication No. WO 95/24209 (PCT/US95/03125), all of which are incorporated herein by reference.

Biologically active variants of BPI (BPI variants) include but are not limited to recombinant hybrid fusion proteins, comprising BPI holoprotein or biologically active fragment thereof and at least a portion of at least one other polypeptide, or dimeric forms of BPI variants. Examples of such hybrid fusion proteins and dimeric forms are described in U.S. Pat. No. 5,643,570 and corresponding International Publication No. WO 93/23434 (PCT/US93/04754), which are all incorporated herein by reference and include hybrid fusion proteins comprising, at the amino-terminal end, a BPI protein or a biologically active fragment thereof and, at the carboxy-terminal end, at least one constant domain of an immunoglobulin heavy chain or allelic variant thereof.

Biologically active analogs of BPI (BPI analogs) include but are not limited to BPI protein products wherein one or more amino acid residues have been replaced by a different amino acid. For example, U.S. Pat. Nos. 5,420,019, 5,674,834 and 5,827,816 and corresponding International Publication No. WO 94/18323 (PCT/US94/01235), all of which are incorporated herein by reference, discloses polypeptide analogs of BPI and BPI fragments wherein a cysteine residue is replaced by a different amino acid. A stable BPI protein product described by this application is the expression product of DNA encoding from amino acid 1 to approximately 193 or 199 of the N-terminal amino acids of BPI holoprotein, but wherein the cysteine at residue number 132 is substituted with alanine and is designated rBPI$_{21}$Δcys or rBPI$_{21}$. Production of this N-terminal analog of BPI, rBPI$_{21}$, has been described in Horwitz et al., *Protein Expression Purification*, 8:28–40 (1996). Similarly, an analog consisting of residues 10–193 of BPI in which the cysteine at position 132 is replaced with an alanine (designated "rBPI (10–193)C132A" or "rBPI(10–193)ala$^{132}$") has been described in U.S. Pat. No. 6,013,631, continuation-in-part U.S. application Ser. No. 09/336,402, filed Jun. 18, 1999, and corresponding International Publication No. WO 99/66044 (PCT/US99/13860), all of which are incorporated herein by reference. Other examples include dimeric forms of BPI analogs; e.g. U.S. Pat. Nos. 5,447,913, 5,703,038, and 5,856,302 and corresponding International Publication No. WO 95/24209 (PCT/US95/03125), all of which are incorporated herein by reference.

Other BPI protein products useful according to the methods of the invention are peptides derived from or based on BPI produced by synthetic or recombinant means (BPI-derived peptides), such as those described in International Publication No. WO 97/04008 (PCT/US96/03845), which corresponds to U.S. application Ser. No. 08/621,259 filed Mar. 21, 1996, and International Publication No. WO 96/08509 (PCT/US95/09262), which corresponds to U.S. Pat. No. 5,858,974, and International Publication No. WO 95/19372 (PCT/US94/10427), which corresponds to U.S. Pat. Nos. 5,652,332 and 5,856,438, and International Publication No. WO94/20532 (PCT/US94/02465), which corresponds to U.S. Pat. No. 5,763,567 which is a continuation of U.S. Pat. No. 5,733,872, which is a continuation-in-part of U.S. application Ser. No. 08/183,222, filed Jan. 14, 1994, which is a continuation-in-part of U.S. application Ser. No. 08/093,202 filed Jul. 15, 1993 (corresponding to International Publication No. WO 94/20128 (PCT/US94/02401)), which is a continuation-in-part of U.S. Pat. No. 5,348,942, as well as International Application No. PCT/US97/05287, which corresponds to U.S. Pat. No. 5,851,802, the disclosures of all of which are incorporated herein by reference. Methods of recombinant peptide production are described in U.S. Pat. No. 5,851,802 and International Publication No. WO97/35009 (PCT/US97/05287), the disclosures of which are incorporated herein by reference.

Exemplary BPI protein products include recombinantly-produced N-terminal analogs or fragments of BPI, especially those having a molecular weight of approximately between 20 to 25 kD such as rBP$_{21}$, rBPI$_{23}$, rBPI(10–193) C132A, (rBPI(10–193)ala$^{132}$), dimeric forms of these N-terminal polypeptides (e.g., rBPI$_{42}$ dimer), or BPI-derived peptides. Exemplary BPI-derived peptides include XMP.391 (SEQ ID NO: 4), XMP.416 (SEQ ID NO: 5) or XMP.445 (SEQ ID NO: 6) [the structure and activity of which are described in co-owned, co-pending U.S. Ser. No. U.S. Ser. No. 09/406,243 filed Sep. 24, 1999, incorporated herein by reference].

The administration of BPI protein products is preferably accomplished with a pharmaceutical composition comprising a BPI protein product and a pharmaceutically acceptable diluent, adjuvant, or carrier. The BPI protein product may be administered without or in conjunction with known surfactants or other therapeutic agents. A stable pharmaceutical composition containing BPI protein products (e.g., rBPI$_{23}$) comprises the BPI protein product at a concentration of 1 mg/ml in citrate buffered saline (5 or 20 mM citrate, 150 mM NaCl, pH 5.0) comprising 0.1 % by weight of poloxamer 188 (Pluronic F-68, BASF Wyandotte, Parsippany, N.J.) and 0.002% by weight of polysorbate 80 (Tween 80, ICI Americas Inc., Wilmington, Del.). Another stable pharmaceutical composition containing BPI protein products (e.g., rBPI$_{21}$) comprises the BPI protein product at a concentration of 2 mg/ml in 5 mM citrate, 150 mM NaCl, 0.2% poloxamer 188 and 0.002% polysorbate 80. Such preferred combinations are described in U.S. Pat. Nos. 5,488,034, 5,696,090 and 5,955,427 and corresponding International Publication No. WO 94/17819 (PCT/US94/01239), the disclosures of all of which are incorporated herein by reference. As described in U.S. Pat. No. 5,912,228 and corresponding International Publication No. WO96/21436 (PCT/US96/01095), all of which are incorporated herein by reference, other poloxamer formulations of BPI protein products with enhanced activity may be utilized, optionally with EDTA.

A further aspect of the invention provides methods for the rational design of molecules that function like antimicrobial BPI protein products. For example, peptides or other organic molecules may be synthesized that mimic the structure and function of BPI-derived peptides with antibacterial activity. The molecules thus designed may be screened according to any of the assays described above. Methods of treating infection using such molecules are also contemplated.

Yet a further aspect of the invention provides methods for identifying compounds that alone exhibit no antimicrobial activity, e.g., due to insufficient ability to penetrate the target cell wall or membrane, but that act as antimicrobial compounds when administered in conjunction with BPI-derived peptides. These compounds are identified by screening them in combination with BPI-derived peptides according to any of the assays described above.

Other aspects and advantages of the present invention will be understood upon consideration of the following illustrative examples. Example 1 addresses the effect of two BPI-derived peptides, XMP.391 (SEQ ID NO: 4) and XMP.445 (SEQ ID NO: 6), on fungal cells with the tetrazolium metabolic oxidation-reduction indicator dye, Alamar Blue™. Example 2 addresses the effect of a variety of BPI protein products and ciprofloxacin on bacteria with Alamar Blue™.

EXAMPLE 1

Effect of Antifungal Compounds on Fungal Cells with Alamar Blue™

Alamar Blue™ is an indicator dye formulated to measure quantitatively the proliferation of a variety of human or animal cells, bacteria, or fungi. It consists of an oxidation-reduction (REDOX) indicator that yields colorimetric and fluorimetric changes in response to metabolic activity (electron transport activity).

The relative effect of two BPI-derived peptides, XMP.391 (SEQ ID NO: 4) and XMP.445 (SEQ ID NO: 6), and the antifungal compound amphotericin B on fungal cells with the metabolic oxidation-reduction indicator dye Alamar Blue™ [AccuMed Int'l, Westlake, Ohio] was assessed as follows.

Candida albicans were grown in 75 mL Sabouraud's dextrose broth (SDB) for 5 hours at 30° C. Cells were pelleted by centrifiguation for 5 minutes in a Sorvall RT6000B centrifuge at 3,000 rpm (1500×g) and resuspended in 15 mL of fresh SDB. A 1:10 dilution of this suspension was used for an $OD_{570\,nm}$ detennination. One OD unit is equivalent to $1×10^7$ CFU/mL. Cells were adjusted to a concentration of $2×10^7$ CFU/mL.

Test compounds XMP.391, XMP.445 and Amphotericin B (AMB) were two-fold serially diluted in SDB from a concentration of 128 μg/mL in a 96-well plate. This was done in triplicate with each well containing a volume of 100 μL. An equal volume of the yeast suspension was added to each well. This resulted in a final concentration of Candida of $1×10^7$ cells/mL, and final dilutions of the test compounds starting from a concentration of 64 μg/mL.

Alamar Blue™ was added at 20 μL per well and the initial (t=0) fluorescence readings were performed in a Molecular Devices SpectraMax Gemini plate reader. The excitation wavelength was 544 nm and the emission wavelength was measured at 590 nm. The plate was incubated at 37° C. and additional readings at 15, 30, 45 and 60 minutes were performed. Metabolic oxidation-reduction activity is detected by an increase in fluorescence emission.

Figure 2:
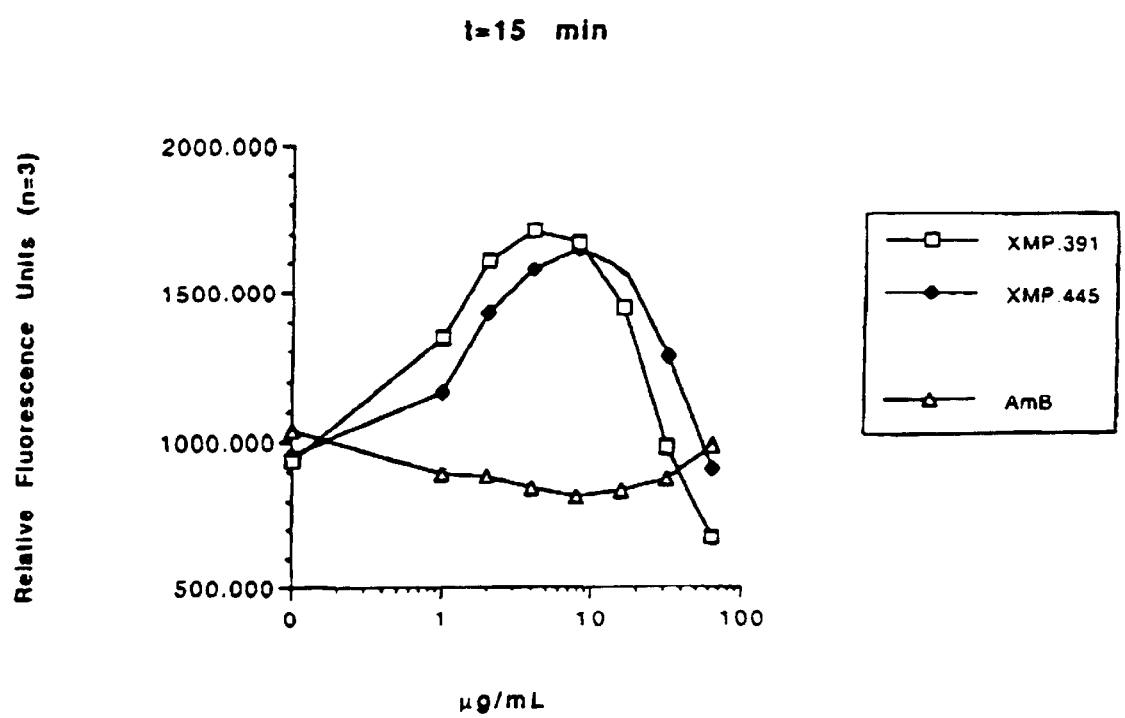
Figure 3:
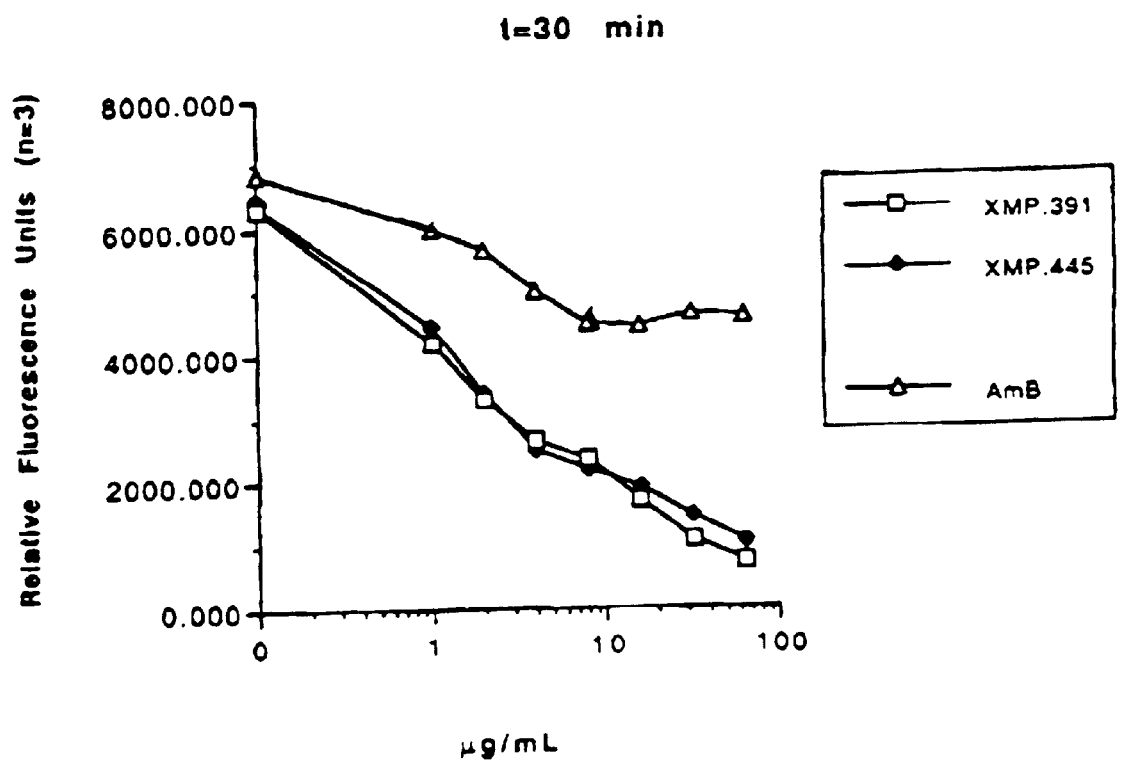
Figure 4:
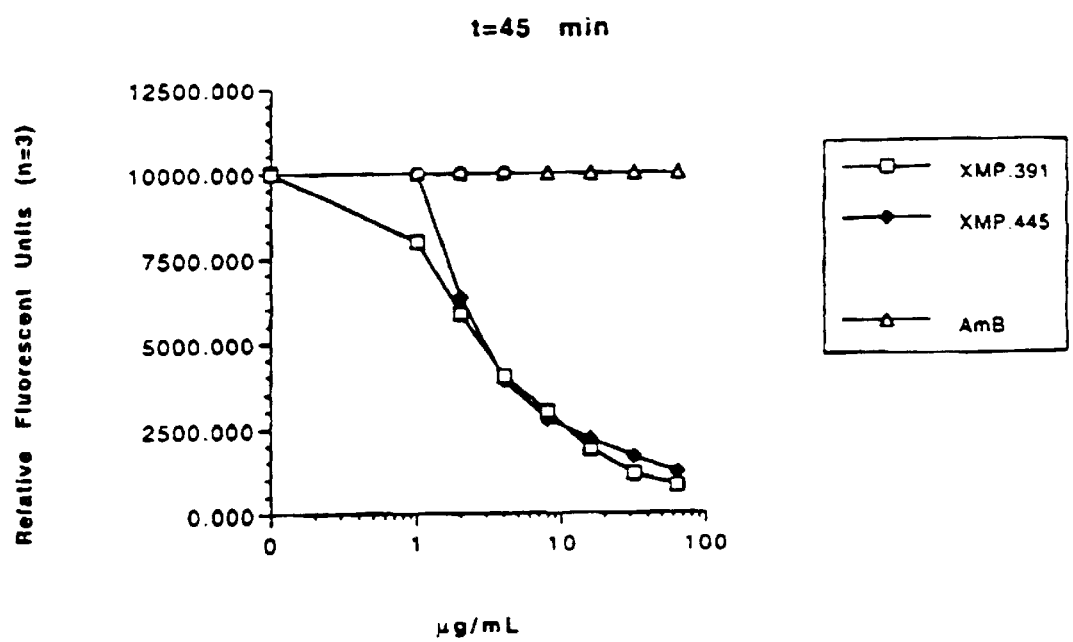
Figure 5:
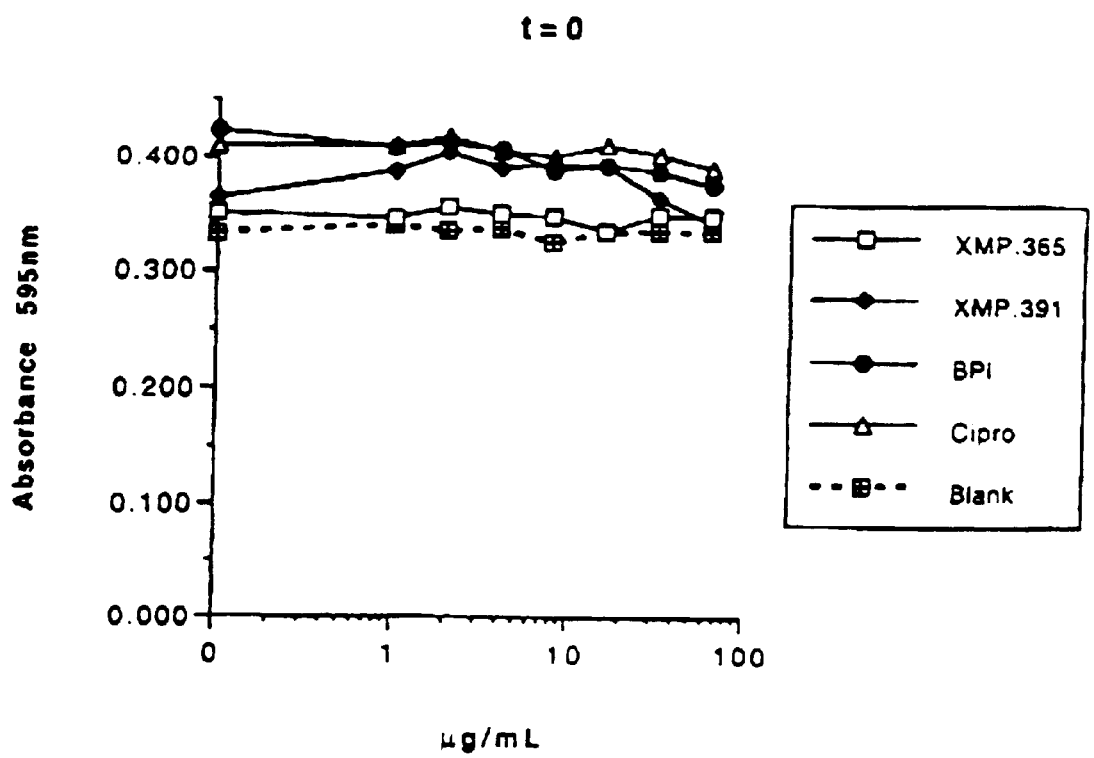
FIGS. 5, 6, 7 and 8 depict the effect of $rBPI_{21}$ and ciprofloxacin on bacteria treated with Alamar Blue™ at 0, 30, 60, 90 and 120 minutes in a calorimetric assay.

Results of the 0, 15, 30 and 45 minute time points are displayed in FIGS. 1, 2, 3 and 4, respectively. Results for treated cells at 45 and 60 minutes were similar. The characteristic pattern or "fingerprint" of BPI protein products is best illustrated in FIG. 2, which shows the increased activity of BPI protein product-treated cells relative to untreated control cells (cells with a 0 concentration of test compound). In contrast, amphotericin B treatment did not show the "fingerprint."

Additional experiments at room temperature produced similar results.

EXAMPLE 2

Effect of Antibacterial Compounds on Bacteria with Alamar Blue™

The relative effect of three antibacterial BPI protein products, XMP.365 (SEQ ID NO: 3), XMP.391 (SEQ ID NO: 4) and $rBPI_{21}$, and the antibiotic ciprofloxacin on bacteria with Alamar Blue™ was assessed as follows.

E. coli (ATCC strain 8739) was incubated at 37° C. in 5 mL cation-adjusted Mueller Hinton Broth (CAMHB) for 3 hours to attain log phase growth. The bacteria were pelleted in a Sorvall RT6000B centrifuge for 5 minutes at 3,000 rpm (1.500×g ) and resuspended in 5 mL of fresh CAMHB. A 1:10 dilution was performed for an $OD_{570\,nm}$ determination. One OD unit equals $1.25×10^9$ CFU/mL. The bacterial suspension was adjusted to $1×10^8$ CFU/mL.

Test compounds XMP.365, XMP.391, $rBPI_{21}$ and ciprofloxacin were two-fold serially diluted in CAMHB from a concentration of 128 μg/mL in a 96-well plate. This was done in triplicate with each well containing a volume of 100 μL. An equal volume of the bacterial suspension was added to each well. This resulted in a final concentration of E. coli of $5×10^7$ /mL, and final dilutions of the test compounds starting from a concentration of 64 μg/mL. Alamar Blue™ was added at 20 μL per well. The "Blank" contained media and Alamar Blue™ only, without cells.

$OD_{595\,nm}$ readings were performed in a Molecular Devices plate reader. This required that samples be centrifuged to pellet bacteria and related debris which would contribute to the $OD_{595\,nm}$ reading. 150 μL were removed from the wells at various timepoints, centrifuged (2 minutes, 2,000 rpm) and 50 μL of supernatant was carefully transferred to a fresh 96-well plate for the reading. Timepoints were read at 0, 30, 60, 90 and 120 minutes. Metabolic oxidation-reduction activity is detected by an increase in OD in this colorimetric assay.

Alternatively, fluorescence readings may be performed in a Molecular Devices SpectraMax Gemini plate reader as described above in Example 1.

Figure 6:
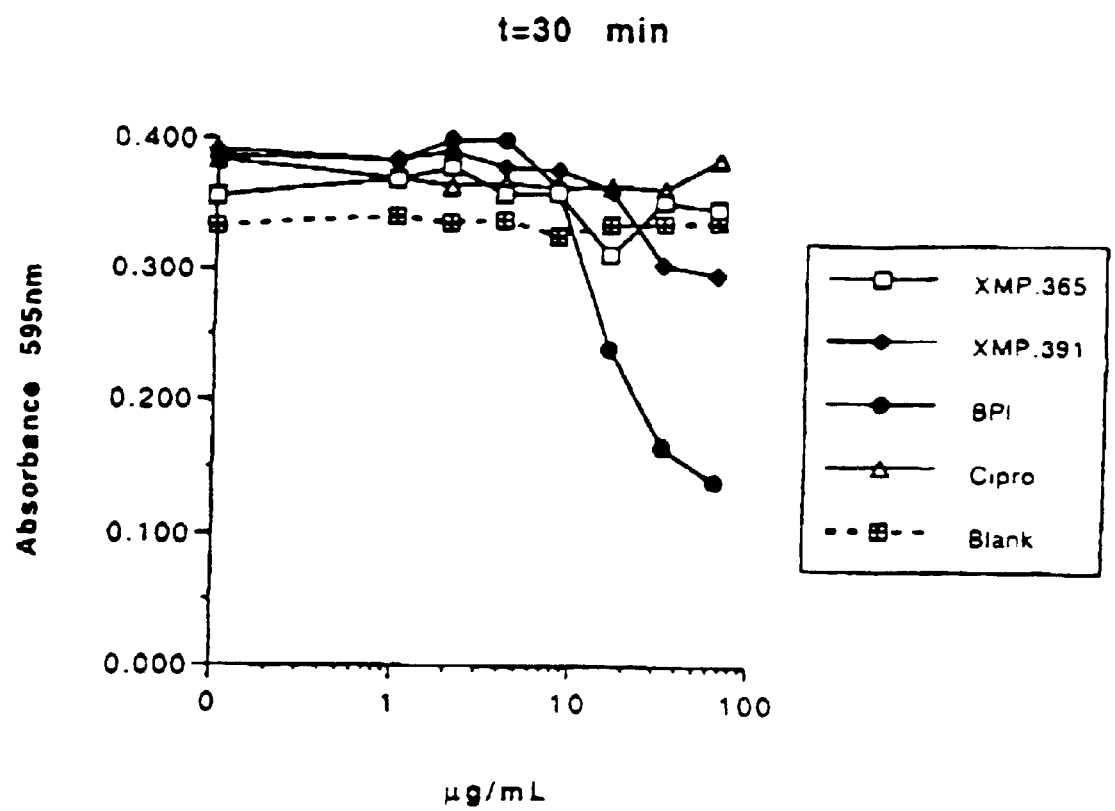
Figure 7:
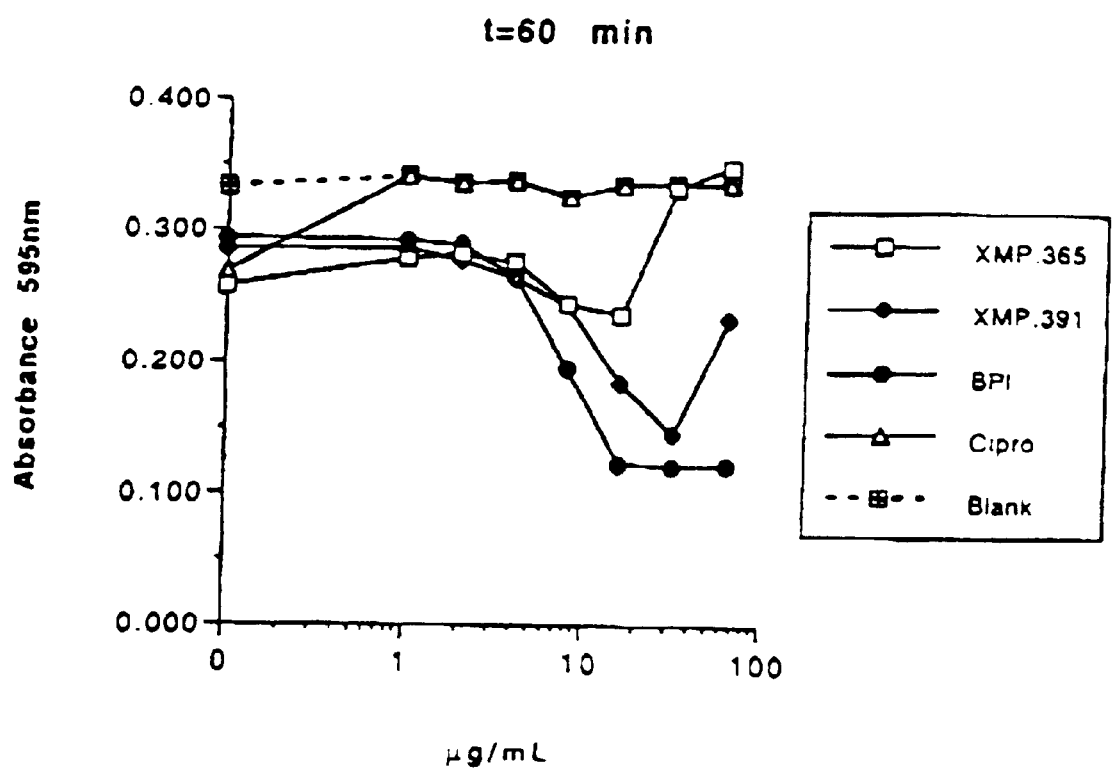
Figure 8:
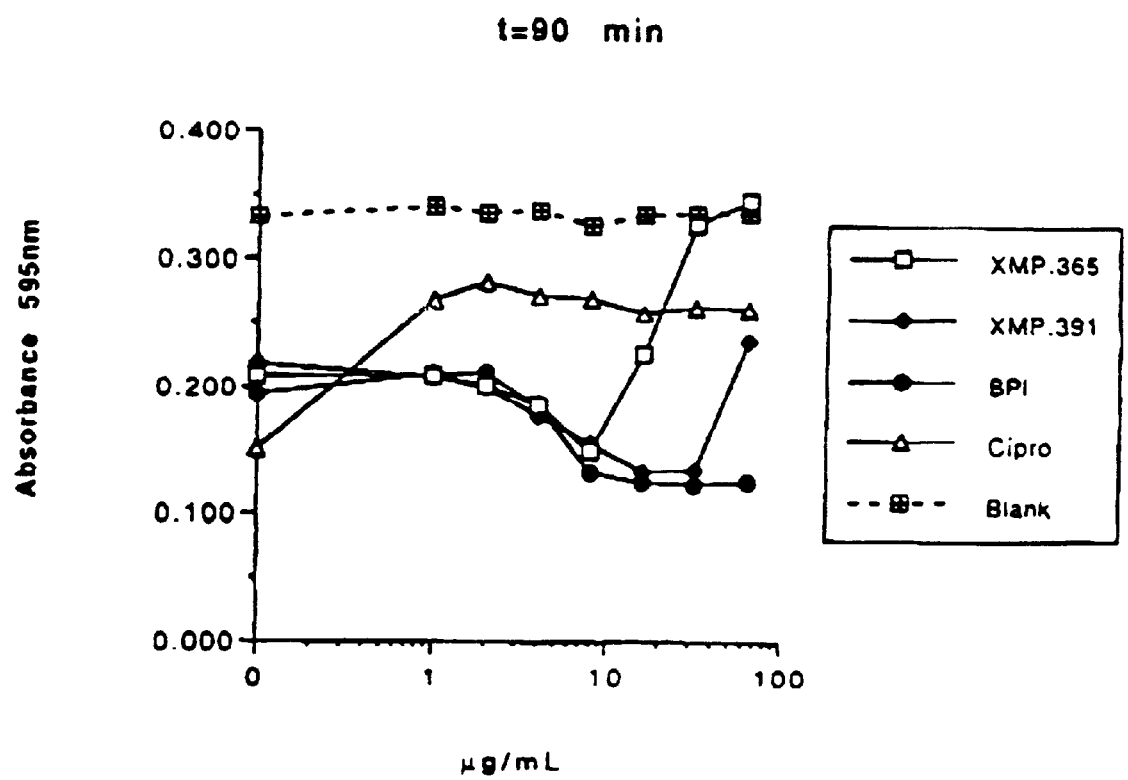

Results of the 0, 30, 60 and 90 time points are displayed in FIGS. 5, 6, 7 and 8, respectively. Results for treated cells at 90 and 120 minutes were similar. The characteristic pattern or "fingerprint" is best illustrated in FIG. 6, which shows the increased activity of BPI protein product-treated cells relative to untreated control cells (cells with a 0 concentration of test compound). In contrast, ciprofloxacin treatment did not show the "fingerprint."

Numerous modifications and variations of the above-described invention are expected to occur to those of skill in the art. Accordingly, only such limitations as appear in the appended claims should be placed thereon.

What is claimed are:

1. A method of identifying antimicrobal compound comprising the steps of:
   (a) contacting a microbial cell with a metabolic activity oxidation-reduction indicator dye in the presence and absence of test compound, and
   (b) detecting apparent increased metabolic activity in the presence of the test compound relative to metabolic activity in the absence of the test compound, despite onset of loss or reduction of microbial cell viability.

2. A method of identifying an antifungal compound comprising the steps of:
   (a) contacting a fungal cell with a metabolic; activity oxidation-reduction indicator dye in the presence and absence of test compound, and
   (b) detecting apparent increased metabolic activity in the presence of the test compound relative to metabolic activity in the absence of the test compound, despite onset of loss or reduction of fungal cell viability.

3. A method of identifying an antibacterial compound comprising the steps of:
   (a) contacting a bacterial cell with a metabolic activity oxidation-reduction indicator dye in the presence and absence of test compound, and
   (b) detecting apparent increased metabolic activity in the presence of the test compound relative to metabolic activity in the absence of the test compound, despite onset of loss or reduction of bacterial cell viability.

4. The method of any one of claims 1 through 3 further comprising the steps of:
   (a) contacting a mammalian cell with said metabolic oxidation-reduction indicator dye in the presence and absence of test compound, and
   (b) detecting no substantial difference in dye signal in the presence and absence of test compound.

5. The method of any one of claims 1 through 3 wherein said metabolic oxidation-reduction indicator dye is a tetrazolium dye.

6. The method of any one of claims 1 through 3 further comprising the step of assaying said test compound for the ability to inhibit growth of microbial cells or to kill microbial cells.

7. The method of any one of claims 1 through 3 further comprising the step of assaying said test compound for oral availability or oral activity.

8. The method of claim 4 further comprising the step of assaying said test compound for oral availability or oral activity.

* * * * *

UNITED STATES PATENT AND TRADEMARK OFFICE
CERTIFICATE OF CORRECTION

PATENT NO.   : 6,436,660 B1
DATED        : August 20, 2002
INVENTOR(S)  : Little, II It is certified that error appears in the above-identified patent and that said Letters Patent is hereby corrected as shown below:

Column 29,
Line 40, after "...fungal cell with a" please delete "metabolic;" and insert -- metabolic -- in its place.

Signed and Sealed this

Eleventh Day of March, 2003

JAMES E. ROGAN
*Director of the United States Patent and Trademark Office*